(12) United States Patent
Schuster

(10) Patent No.: US 12,383,722 B2
(45) Date of Patent: *Aug. 12, 2025

(54) NEXT GENERATION TOTAL ARTIFICIAL HEART

(71) Applicant: SYNCARDIA SYSTEMS, LLC, Tucson, AZ (US)

(72) Inventor: Matthew Scott Schuster, Tucson, AZ (US)

(73) Assignee: SYNCARDIA SYSTEMS, LLC, Tucson, AZ (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/886,718

(22) Filed: Sep. 16, 2024

(65) Prior Publication Data

US 2025/0001157 A1 Jan. 2, 2025

Related U.S. Application Data

(60) Division of application No. 18/432,598, filed on Feb. 5, 2024, now Pat. No. 12,121,711, which is a continuation of application No. 17/779,058, filed as application No. PCT/US2020/060785 on Nov. 16, 2020, now Pat. No. 11,918,798.

(60) Provisional application No. 62/938,733, filed on Nov. 21, 2019.

(51) Int. Cl.
*A61M 60/196* (2021.01)
*A61M 60/476* (2021.01)

(52) U.S. Cl.
CPC ........ *A61M 60/196* (2021.01); *A61M 60/476* (2021.01)

(58) Field of Classification Search
CPC .......................... A61M 60/196; A61M 60/476
See application file for complete search history.

(56) References Cited

U.S. PATENT DOCUMENTS

| | | | |
|---|---|---|---|
| 4,512,726 A | 4/1985 | Strimling | |
| 4,750,903 A | 6/1988 | Cheng | |
| 4,786,240 A | 11/1988 | Koroly et al. | |
| 4,976,730 A | 12/1990 | Kwan-Gett | |
| 5,135,539 A | 8/1992 | Carpentier | |
| 5,271,746 A | 12/1993 | Pol et al. | |
| 5,674,281 A | 10/1997 | Snyder | |
| 6,342,072 B1 | 1/2002 | Wartelle et al. | |
| 9,561,595 B1 | 2/2017 | Dellon | |
| 11,918,798 B2 * | 3/2024 | Schuster | A61M 60/446 |

(Continued)

FOREIGN PATENT DOCUMENTS

WO WO-2016020219 A1 * 2/2016 .......... A61M 1/1081

OTHER PUBLICATIONS

PCT International Search Report and Written Opinion, PCT/US2020/060785, Apr. 1, 2021, 17 pages.

(Continued)

*Primary Examiner* — Suzette J Gherbi
(74) *Attorney, Agent, or Firm* — Quarles & Brady LLP; Yakov S. Sidorin

(57) ABSTRACT

A total artificial heart system includes at least one artificial ventricle coupled to (or capable of being coupled to) a chamber or a vessel of a human heart, and at least one drive system coupled to the artificial ventricle, the drive system including at least one implanted electric motor. The drive system causes the artificial ventricle to contract and expand.

5 Claims, 18 Drawing Sheets

(56) References Cited

U.S. PATENT DOCUMENTS

| | | | | |
|---|---|---|---|---|
| 12,121,711 B2* | 10/2024 | Schuster | ............. | A61M 60/196 |
| 2001/0003802 A1 | 6/2001 | Vitale | | |
| 2004/0152944 A1 | 8/2004 | Medvedev et al. | | |
| 2005/0135948 A1 | 6/2005 | Olsen et al. | | |
| 2009/0110496 A1 | 4/2009 | Veres | | |
| 2012/0095280 A1 | 4/2012 | Timms | | |
| 2013/0041460 A1 | 2/2013 | Heilman et al. | | |
| 2014/0371849 A1 | 12/2014 | Orejola et al. | | |
| 2016/0235899 A1 | 8/2016 | Yu et al. | | |
| 2017/0224894 A1* | 8/2017 | Najar | .................. | A61M 60/196 |
| 2019/0209752 A1 | 7/2019 | Nyikos et al. | | |
| 2019/0331236 A1* | 10/2019 | Singh | .................. | A61M 60/178 |
| 2024/0009444 A1* | 1/2024 | Schuster | ............. | A61M 60/268 |
| 2024/0207599 A1* | 6/2024 | Schuster | ............. | A61M 60/258 |

OTHER PUBLICATIONS

European Patent Office, Extended Search Report, Application No. 20890347.6, Feb. 15, 2024, 11 pages.

* cited by examiner

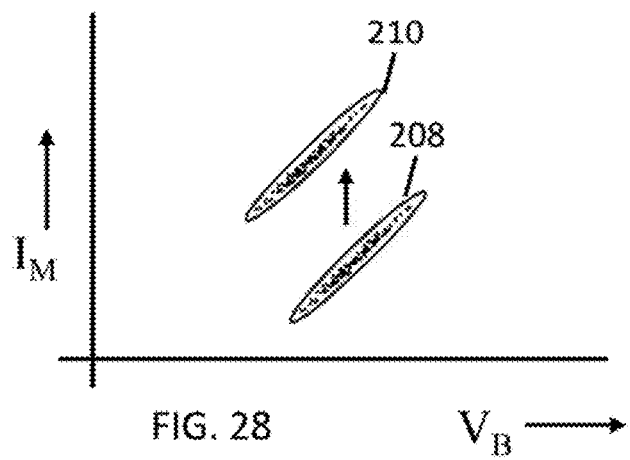
FIG. 28
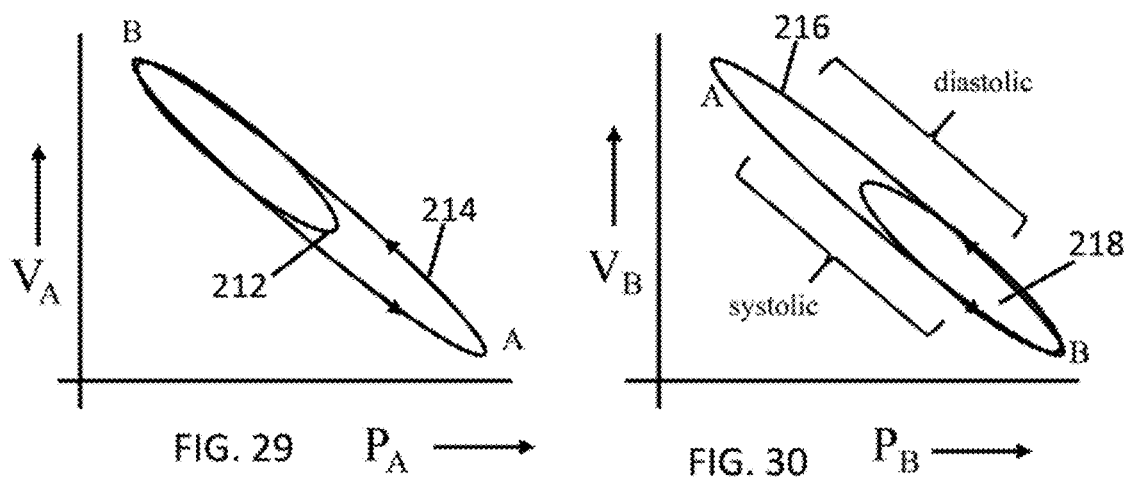
FIG. 29
FIG. 30
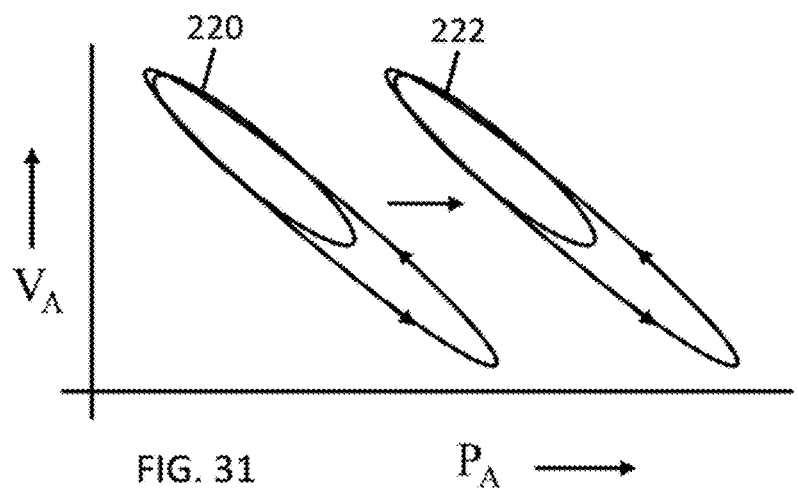
FIG. 31

NEXT GENERATION TOTAL ARTIFICIAL HEART

CROSS-REFERENCE TO RELATED APPLICATIONS

This US patent application is a divisional from the U.S. patent application Ser. No. 18/432,598 filed on Feb. 5, 2024 and now granted as U.S. Pat. No. 12,121,711, which is a continuation from the U.S. patent application Ser. No. 17/779,058 filed on May 23, 2022 and now granted as U.S. Pat. No. 11,918,798, which is a national phase of the International Application No. PCT/US2020/060785 filed on Nov. 16, 2020 and now published as WO 2021/101848, which in turn designates the United States and claims priority from the U.S. Provisional Patent Application No. 62/938,733 filed on Nov. 21, 2019. The disclosure of each of the above-identified patent documents is incorporated herein by reference for all purposes.

TECHNICAL FIELD

The subject matter described herein relates to apparatuses, systems, and methods for portably actuating an electric motor-driven artificial heart.

RELATED ART

The heart is the muscle that drives the cardiovascular system in humans and other living beings. Acting as a pump, the heart moves blood throughout the body to provide oxygen, nutrients, hormones, and to remove waste products. The blood follows two separate pathways in the human body, the so-called pulmonary and systemic circulatory circuits. In the pulmonary circuit, the heart pumps blood first to the lungs to release carbon dioxide and bind oxygen, and then back to the heart. Thus, oxygenated blood is constantly being supplied to the heart. In the systemic circuit, the longer of the two, the heart pumps oxygenated blood through the rest of the body to supply oxygen and remove carbon dioxide, the byproduct of metabolic functions carried out throughout the body. The heart supplies blood to the two circuits with pulses generated by the orderly muscular contraction of its walls.

In order to keep blood moving through these two separate circulatory circuits, the human heart has four distinct chambers that work in pairs. As illustrated in FIG. 1, the heart 10 includes a right atrium 12, a right ventricle 14, a left atrium 16, and a left ventricle 18. One pair of chambers, the right ventricle and left atrium, is connected directly to the pulmonary circuit. In it, de-oxygenated blood from the body is pumped from the right ventricle 14 to the lungs, where it is oxygenated, and then pumped back to the left atrium 16.

In the systemic circuit, the other pair of chambers pumps the oxygenated blood through body organs, tissues and bones. The blood moves from the left atrium 16, where it flows from the lungs, to the left ventricle 18, which in turn pumps the blood throughout the body and all the way back to the right atrium 12. The blood then moves to the right ventricle 14 where the cycle is repeated. In each circuit, the blood enters the heart through an atrium and leaves the heart through a ventricle.

Thus, the ventricles 14, 18 are essentially two separate pumps that work together to move the blood through the two circulatory circuits. Four check valves control the flow of blood within the heart and prevent flow in the wrong direction. A tricuspid valve 20 controls the blood flowing from the right atrium 12 into the right ventricle 14. Similarly, a bicuspid valve 22 controls the blood flowing from the left atrium 16 into the left ventricle 18. Two semilunar valves (pulmonary 24 and aortic 26) control the blood flow leaving the heart toward the pulmonary and systemic circuits, respectively. Thus, in each complete cycle, the blood is pumped by the right ventricle 14 through the pulmonary semilunar valve 24 to the lungs and back to the left atrium 16. The blood then flows through the bicuspid valve 22 to the left ventricle 18, which in turn pumps it through the aortic semilunar valve 26 throughout the body and back to the right atrium 12. Finally, the blood flows back to the right ventricle 14 through the tricuspid valve 20 and the cycle is repeated.

When the heart muscle squeezes each ventricle, it acts as a pump that exerts pressure on the blood, thereby pushing it out of the heart and through the body. The blood pressure, an indicator of heart function, is measured when the heart muscle contracts as well as when it relaxes. The so-called systolic pressure is the maximum pressure exerted by the blood on the arterial walls when the left ventricle of the heart contracts forcing blood through the arteries in the systemic circulatory circuit. The so-called diastolic pressure is the lowest pressure on the blood vessel walls when the left ventricle relaxes and refills with blood. Healthy blood pressure is considered to be about 120 millimeters of mercury systolic and 80 millimeters of mercury diastolic (usually presented as 120/80).

Inasmuch as the function of the circulatory system is to service the biological needs of all body tissues (i.e., to transport nutrients to the tissues, transport waste products away, distribute hormones from one part of the body to another, and, in general, to maintain an appropriate environment for optimal function and survival of tissue cells), the rate at which blood is circulated by the heart is a critical aspect of its function. The heart has a built-in mechanism (the so-called Frank-Starling mechanism) that allows it to pump automatically whatever amount of blood flows into it. Such cardiac output in a healthy human body may vary from about 4 to about 15 liters per minute (LPM), according to the activity being undertaken by the person, at a heart rate that can vary from about 50 to about 180 beats per minute.

Several artificial devices have been developed over the years to supplement or replace the function of a failing heart in patients. These include devices developed by companies as well as research institutions such as the Berlin Heart Institute, the Pennsylvania State University, the University of Utah, the Cleveland Clinic Foundation, the University of Perkinje (in Bruno, Czechoslovakia), the University of Tokyo, the Thoratec Corporation, Abiomed Inc., Novacor, and Symbion Inc. Typically, these artificial devices consist of pumps that aim at duplicating the required pumping functions of the left and right human ventricles. One method of actuation for these pumps has been through the pneumatic action of an external mechanism. See, for example, U.S. Pat. Nos. 4,611,578 and 5,766,207. Periodic pulses of compressed air drive the pumps at the desired pressure and rate of cardiac output. A moderate vacuum may be applied between pulses to allow more rapid refilling of the ventricles with blood flowing from the respective atrium.

The pneumatic drivers used to date for driving all artificial hearts have been cumbersome and inadequate for affording patients any degree of independent mobility. They employ compressors, vacuum pumps, and air tanks coupled to electrically actuated valves, all of which amounts to a large and heavy apparatus that can only be transported on wheels and with considerable effort. Therefore, many attempts have been made during the last two decades to produce a portable driver for these devices. However, because of the complexity of the required functionality and the hardware necessary to produce it, pneumatic heart drivers continue to be bulky, require frequent maintenance, and often provide air pulses that do not match the performance of the larger drivers they are meant to replace. Even at the approximate weight of 15 pounds and size of about 0.7 cubic feet achieved so far, pneumatic drivers remain unwieldy and substantially not portable for a patient who is kept alive by an artificial heart.

In essence, a portable driver needs to be reliable, durable, easy to use, and sufficiently simple in design to be affordable. Unfortunately, each of these requirements contributes to the complexity of the design, which in turn has produced devices that are not sufficiently small and light-weight to be manageable in the hands of a patient.

Furthermore, it is essential that the pneumatic driver be able to provide the correct pressure balance between the left and right ventricles of the artificial heart to ensure the proper operating pressure to the pulmonary and systemic circuits regardless of the speed of operation. Typically, this requires that the driver be able to operate so as to maintain, on average, a right atrial pressure of about 9 mmHg, a mean pulmonary artery pressure of about 35 mmHg, a left atrial pressure of about 10 mmHg, and a mean aortic pressure of about 95 mmHg.

This need to provide different operating pressures to the right and left chambers (ventricles) of the artificial-heart device has not been met heretofore with a simple design suitable for a portable driver. For example, the blood pump described in U.S. Pat. No. 4,611,578 includes a configuration wherein two reciprocating pistons in a common cylinder may be operated alternatively to provide redundancy or independently to actuate two separate pneumatically driven blood pumps. This issue is not addressed in the patent, but it describes a sophisticated control system that arguably could be used to provide the correct operating pressure to each chamber of the artificial heart. However, the complex and multi-component structure of the device necessarily requires a relatively heavy and large apparatus, though described as portable. The commercially available module weighs about 25 pounds and is approximately 0.6 cubic feet in volume.

U.S. Pat. No. 5,766,207 describes another portable pneumatic driver for ventricular assist devices that could also be adapted for an artificial heart. The single pump of the invention could be used to drive both ventricles of an artificial heart, but only at the same pressure and volume rate. Thus, this device, even if modified to meet the other requirements of a portable artificial-heart driver, would not be suitable as an alternative to the stationary modules currently in use.

In one or more lighter options, a system may include a portable case weighing about fifteen (15) pounds, and including one or more compressors acting as drivers for the pneumatic system. Because this arrangement involves pushing pulses of air through tubes into and out of the artificial heart, high fluid and/or backpressure losses occur resulting in limited battery life (i.e., due to the high amperage or current drawn by the compressors). For example, in one or more systems, the device runs for approximately 2 hours before batteries need to be replaced or recharged. In addition, the patient is required to carry the system, which limits the activities the patient may undertake due to at least one hand or arm having to carry the system. Such systems may also include hundreds of individual parts, which may have an impact on the reliability of the system. In addition, in order to approximate the displacement of blood, the volumetric airflow through the system (which itself presents uncertainty) needs to be determined.

Other systems use impellers (or rotational pumping devices) to directly pressurize and pump the blood. However, impactions and/or contact between the impeller and the blood create high sheer stresses, which can damage the blood.

Therefore, the current options available to patients do not meet the desired characteristics, which include providing a mobile, highly reliable, light-weight, manageably-sized, and portable system for a patient in need of a heart transplant.

SUMMARY OF THE INVENTION

The present disclosed embodiments include apparatus, systems, and methods for enabling a next generation total artificial heart, which provides enhanced patient flexibility and case of use. The next generation total artificial heart includes artificial ventricles which connect to existing chambers and/or vessels of a human heart. Each artificial ventricle is connected to a drive system that includes an electrical motor implanted in the patient's chest cavity. The electrical motor drives a cam and follower system that is used to expand and contract the artificial ventricles. One or more groups of wires connect the implanted electrical motor (inside the patient's body) to an external power supply (outside the patient's body), which is lightweight, easy to carry or wear, and easy to operate.

In one aspect, the invention is directed to a total artificial heart system including: a right artificial ventricle coupled to a pulmonary artery; a left artificial ventricle coupled to a left atrium; a first drive system coupled to the right artificial ventricle, the first drive system including a first implanted electric motor; and a second drive system coupled to the left artificial ventricle, the second drive system comprising a second implanted electric motor. In some embodiments, the system includes a first wire coupling the first implanted electric motor to an external power supply; and a second wire coupling the second implanted electric motor to the external power supply. In some embodiments, the external power supply is external to the body of a patient. In some embodiments, each of the right artificial ventricle, the left artificial ventricle, the first drive system, and the second drive system are internal to the body of the patient. In some embodiments, a portion of the first wire is internal to a body of a patient, and a portion of the first wire is external to the body of a patient. In some embodiments, the first drive system includes a stator assembly including at least one housing. In some embodiments, the first drive system further includes a rotorcam disposed about the at least one housing of the stator assembly, and the rotorcam is electrically coupled to the stator assembly.

In some embodiments, the system includes a cam follower mechanically coupled to both the stator assembly and the rotorcam. In some embodiments, the rotorcam acts as both a cam in a cam and follower system, as well as a rotor in an electrical motor assembly. In some embodiments, the rotorcam comprises at least one permanent magnet. In some embodiments, the rotorcam, the stator assembly, and/or the cam follower is coated with a coating. In some embodiments, the coating comprises at least one biocompatible material. In some embodiments, the coating comprises a segmented polyurethane solution, silicone rubber, thermoplastic elastomers (TPE), and/or polyvinyl chloride (PVC). In some embodiments, the right artificial ventricle and/or the left artificial ventricle includes a segmented polyurethane solution, silicone rubber, thermoplastic elastomers (TPE), and/or polyvinyl chloride (PVC). In some embodiments, the first implanted electric motor and the second implanted electric motor include a brushless direct current (BLDC) electric motor. In another aspect, the invention is directed to a total artificial heart system including: at least one artificial ventricle capable of being coupled to a chamber and/or a vessel of a human heart. The system further includes at least one drive system coupled to the artificial ventricle and including at least one implanted electric motor. The drive system causes the artificial ventricle to contract and expand.

In some embodiments, the drive system includes at least one cam and follower system. In some embodiments, the system includes an external power supply and at least one wire coupling the implanted electric motor to the external power supply. In some embodiments, the external power supply includes a control interface allowing a patient to adjust a cardiac output of the total artificial heart system. In another aspect, the invention is directed to a total artificial heart system including: at least one artificial ventricle capable of being coupled to a chamber and/or a vessel of a human heart; at least one drive system coupled to the artificial ventricle and including at least one implanted electric motor; and at least one diaphragm defining a boundary between the artificial ventricle and the drive system.

In some embodiments, on a ventricle side, the diaphragm contacts human blood, and on a drive system side, the diaphragm contacts air. In another aspect, the invention is direct to a drive system for a total artificial heart including a stator assembly; a rotorcam mechanically and electrically coupled to the stator assembly; and a cam follower mechanically coupled to both the stator assembly and the rotorcam. In some embodiments, the system includes at least one spring coupling the cam follower to the stator assembly. In some embodiments, the stator assembly includes a housing with a shaped cross-section. The cam follower includes a shaft with a shaped-cross section matching the shaped cross-section of the housing, and the shaft is disposed within the housing. In some embodiments, the shaft moves longitudinally within the housing. In some embodiments, the shaped cross-section of both the housing and the shaft includes at least one of a triangular cross-section, a square cross-section, an elliptical cross-section, a pentagonal cross-section, a hexagonal cross-section, and a rectangular cross-section.

In some embodiments, the rotorcam includes: a center bore concentric about a centerline of the rotorcam; and a ramp radially disposed around the center bore. In some embodiments, the ramp includes at least one drop-off. In some embodiments, the ramp includes an inclined portion. In some embodiments, the ramp comprises a flat portion disposed between the inclined portion and the drop-off. In some embodiments, the cam follower comprises at least one tooth extending toward the rotorcam and interfacing with the ramp. In some embodiments, the rotorcam includes neodymium iron boron (ND-Fe—B), iron, cobalt, samarium cobalt (SM-Co), aluminum, alnico, bonded Nd—Fe—B, magnetite, ceramic (hard ferrite), ferrite, gadolinium, one or more rare earth elements, strontium, barium, and/or iron (III) oxide.

In some embodiments, the system includes at least one proximity sensor disposed within the stator assembly and/or the cam follower. The proximity sensor detects the relative position of the cam follower to the stator assembly. In some embodiments, the system includes at least one damper disposed within the housing. In some embodiments, the system includes at least one pressure sensor disposed on or within the stator assembly and/or the rotorcam. In some embodiments, the rotorcam includes a center bore, the stator assembly includes a cylindrical housing, and the cylindrical housing is disposed within the center bore such that rotorcam extends circumferentially around, and radially outward of, the cylindrical housing.

In some embodiments, the system includes a retaining rim disposed around the top of the cylindrical housing, the retaining rim allowing the rotorcam to rotate about the cylindrical housing while preventing the rotorcam from translating longitudinally. In some embodiments, the stator assembly includes a cylindrical housing, the rotorcam is disposed about the cylindrical housing, and a rotation of the rotorcam about the cylindrical housing causes a change in a height of the cam follower. In some embodiments, the cam follower is coupled to at least one artificial ventricle, and the change in the height of the cam follower contracts or expands the artificial ventricle to which the drive system is coupled.

In another aspect, the invention is directed to a drive system for a total artificial heart including: at least one stator assembly; at least one rotorcam coupled to the stator assembly; at least one cam follower coupled to the rotorcam; and at least one artificial ventricle coupled to the cam follower. A change in height of the cam follower causes an expansion of the artificial ventricle. In some embodiments, a magnitude of the expansion of the artificial ventricle is inversely proportional to a rotational speed of the rotorcam. In another aspect, the invention is directed to an electric motor including: an inner stator housing; a plurality of winding groups disposed radially outward of the inner stator housing; an outer stator housing disposed radially outward of the plurality of winding groups; and a rotor disposed radially outward of the outer stator housing.

In some embodiments, the electric motor includes a brushless direct current (BLDC) motor. In some embodiments, the motor includes at least one Hall sensor. In some embodiments, the motor includes at least six (6) winding groups. In some embodiments, each winding group includes one or more longitudinally aligned conductive coil wires.

In some embodiments, the inner stator housing includes a hexagonal housing, and the outer stator housing includes a cylindrical housing. In some embodiments, the rotor includes at least one permanent magnet. In some embodiments, the permanent magnet includes neodymium iron boron (NDFe—B), iron, cobalt, samarium cobalt (SM-Co), aluminum, alnico, one or more rare earth elements, bonded Nd—Fe—B, magnetite, ceramic (hard ferrite), ferrite, gadolinium, strontium, barium, and/or iron (III) oxide.

In some embodiments, the electric motor operates at a power level from about one (1) watt to about ten (10) watts. In another aspect, the invention is directed to an electric motor system including: a stator assembly including: a circular base; at least one housing longitudinally extending from the circular base; and a plurality of winding groups disposed either radially inward of or radially outward of the housing. The motor further includes at least one rotor disposed radially outward of the housing. In some embodiments, the housing includes a hexagonal housing disposed radially inward of the winding groups. In some embodiments, the housing includes a cylindrical housing disposed radially outward of the winding groups. In some embodiments, the rotor includes a cam.

In some embodiments, the system includes at least one power supply electrically coupled to the circular base. In some embodiments, the mobile power supply includes an integral control interface operatively coupled to the stator assembly. In some embodiments, the mobile power supply includes at least one battery disposed within the circular base, and the circular base includes a cylindrical shape. In some embodiments, the integral control interface controls a rotational speed of the rotor. In some embodiments, the integral control interface selectively controls the rotational speed of the rotor within each rotation of the rotor. In some embodiments, the integral control interface selectively adjusts the rotational speed of the rotor within each rotation of the rotor based on a circumferential orientation of rotor. In some embodiments, the integral control interface selectively adjusts the rotational speed of the rotor from a first rotational speed at a first range of circumferential orientations of the rotor to a second rotational speed at a second range of circumferential orientations of the rotor. In some embodiments, the integral control interface selectively adjusts the rotational speed of the rotor from a first rotational speed at a first range of rotor angles to a second rotational speed at a second range of rotor angles.

In another aspect, the invention is directed to a cam and follower system including: at least one rotorcam rotating about a centerline, the rotorcam including at least two angled ramps circumferentially extending around the rotorcam; and at least one cam follower mechanically coupled to the rotorcam. In some embodiments, the two angled ramps include: at least one outer ramp; and at least one inner ramp disposed at a smaller radius than the outer ramp. In some embodiments, the cam follower includes at least two teeth extending toward the rotorcam. Each tooth contacts at least one of the angled ramps.

In some embodiments, the two teeth include exactly two (2) teeth, and the two (2) teeth are circumferentially spaced apart about one-hundred and eighty (180) degrees.

In some embodiments, each of the outer ramp and the inner ramp include at least one drop-off. In some embodiments, the drop-offs are circumferentially spaced apart about one hundred and eighty (180) degrees. In some embodiments, system includes at least three (3) teeth and at least three (3) ramps. In some embodiments, each of outer ramp and the inner ramp include at least one inclined portion. In some embodiments, each of outer ramp and the inner ramp include at least one flat portion disposed between the inclined portion and the drop-off. In some embodiments, each inclined portion circumferentially extends about two hundred and seventy (270) degrees and each flat portion circumferentially extends about ninety (90) degrees. In some embodiments, each inclined portion circumferentially extends around the rotorcam through a first angle, the first angle being from about three-hundred (300) degrees to about three-hundred and sixty (360) degrees. In some embodiments, each flat portion circumferentially extends around the rotorcam through a second angle, the second angle being from about zero (0) degrees to about sixty (60) degrees.

In some embodiments, the rotorcam includes at least one radial gap disposed radially outward of the inner ramp and radially inward of the outer ramp. In some embodiments, the rotorcam includes a center bore disposed radially inward of the inner ramp. In some embodiments, the at least two teeth further include exactly three (3) teeth, and the exactly three (3) teeth are circumferentially spaced apart about one-hundred and twenty (120) degrees from each other.

In another aspect, the invention is directed to a cam and follower system including: at least one rotorcam rotating about a centerline, the rotorcam including at least one contoured lobe extending longitudinally; and at least one cam follower mechanically coupled to the rotorcam. In some embodiments, the cam follower includes at least one follower lobe contoured to match the contoured lobe of the rotorcam. In some embodiments, the rotorcam includes multiple contoured lobes; and the cam follower includes multiple follower lobes. In some embodiments, the system includes an equal number of contoured lobes and follower lobes. In some embodiments, the rotorcam includes at least (4) contoured lobes; and the cam follower includes at least four (4) follower lobes.

In another aspect, the invention is directed to a mobile power supply unit for a total artificial heart including: at least one housing; at least two battery ports disposed within the housing; and at least one group of wires electrically coupling the two battery ports to the total artificial heart. In some embodiments, the total artificial heart is implanted within a human patient. In some embodiments, the group of wires electrically couples the two battery ports to at least one electric motor implanted within a human patient.

In some embodiments, the unit includes a communications module disposed within the housing and communicatively coupling the mobile power supply unit wirelessly to at least one electronic device. In some embodiments, the unit includes at least one display screen displaying a heartrate of the total artificial heart and at least one battery charge level. In some embodiments, the unit includes a heartrate control module. In some embodiments, a user increases or decreases the heartrate of the total artificial heart via the heartrate control module. In some embodiments, the unit includes a volume control module. In some embodiments, a user increases or decreases the volume of blood pumped by the total artificial heart via the volume control module. In another aspect, the invention is directed to a battery charging system for a total artificial heart including: at least one charger housing including at least two battery ports for receiving one or more rechargeable batteries; at least one display screen disposed within the charger housing and displaying at least one battery charge level; and at least one power supply including at least one AC to DC converter and electrically coupled to the two battery ports.

In some embodiments, the system includes at least two rechargeable batteries receiving energy from the battery charging system. The two batteries dissipate energy within a mobile power supply powering the total artificial heart.

In another aspect, the invention is directed to an electronic device including: at least one display screen; application software for tracking the activity of at least one total artificial heart; and at least one communications module wirelessly communicatively coupling the electronic device to a mobile power supply coupled to the total artificial heart. In some embodiments, at least one data parameter transmitted from the mobile power supply to the electronic device is displayed on the display screen. In some embodiments, the data parameter includes a heartrate and/or a blood pressure of at least one patient in which the total artificial heart is implanted. In some embodiments, the data parameter includes a battery charge level and/or a remaining life of at least one battery coupled to the mobile power supply. In some embodiments, the data parameter includes a right ventricle blood volume of at least one patient in which the total artificial heart is implanted, a left ventricle blood volume of the patient in which the total artificial heart is implanted, an operating mode of the total artificial heart, and/or an operating status of the total artificial heart. In some embodiments, the electronic device communicates with a second electronic device on which the application software is installed.

In another aspect, the invention is directed to a total artificial heart system including: at least one artificial ventricle coupled to a vessel and/or a chamber of a heart; at least one drive system coupled to the artificial ventricle and including at least one electric motor; and at least one power supply electrically coupled to the electric motor. The artificial ventricle, the drive system, and the power supply are implanted in the chest cavity of a patient. In some embodiments, the electric motor includes a cylindrical base, and the power supply includes at least one battery. The battery is disposed within the cylindrical base. In some embodiments, the system includes at least one external charging port electrically coupled to the power supply. The external charging port is disposed outside of the body of the patient.

In another aspect, the invention is directed to a method of implanting a total artificial heart including: providing a total artificial heart including at least one electric motor coupled to at least one drive system and at least one wire; implating the total artificial heart within a chest cavity of a patient; and connecting the electric motor to at least one mobile power supply. In some embodiments, the electric motor includes a brushless direct current (BLDC) electric motor. In some embodiments, at least one component of the drive system includes at least one segmented polyurethane solution (SPUS).

In some embodiments, at least one component of the drive system is coated with at least one segmented polyurethane solution (SPUS). In some embodiments, the system includes: at least one stator assembly; at least one rotorcam coupled to the stator assembly; and at least one cam follower coupled to both the stator assembly and the rotorcam. In some embodiments, the rotorcam functions as both a rotor in the electric motor and as a cam in a cam and follower system.

In another aspect, the invention is directed to a method of calibrating a total artificial heart including: setting an initial location of a first Hall sensor within an electric motor of a drive system driving the total artificial heart; setting an initial location of a second Hall sensor within the electric motor; establishing an offset between the initial locations of the first and second Hall sensors; initiating operation of the electric motor; monitoring locations of the first and second Hall sensors; identifying when the offset has altered from an initial offset value; and increasing and/or decreasing an electrical current to the electric motor in order to adjust the offset to a desired value.

In another aspect, the invention is directed to a method operating a total artificial heart including: initiating operation of the total artificial heart; establishing, at a control interface of the total artificial heart, at least one set-point comprising a target heartrate of the total artificial heart for a given activity mode; and changing a cardiac output of the total artificial heart based on at least one data parameter received at the control interface.

In some embodiments, the data parameter includes a blood pressure of a patient in which the total artificial heart is implanted. In some embodiments, the data parameter includes a breathing rate of a patient in which the total artificial heart is implanted. In some embodiments, the data parameter includes a ventricular blood pressure differential of a patient in which the total artificial heart is implanted. In some embodiments, the activity mode includes a resting activity mode. In some embodiments, the activity mode includes a moderate activity mode. In some embodiments, the data parameter includes a vigorous activity mode. In some embodiments, the method includes selecting, at the control interface, at least one activity mode. In some embodiments, the method includes assessing, at the control interface, at least one manual input. In some embodiments, the manual input includes altering a heartrate of the total artificial heart at a heartrate control module coupled to the control interface. In some embodiments, the manual input includes altering a volume of blood pumped by the total artificial heart at a volume control module coupled to the control interface.

Throughout the description, where an apparatus, systems or compositions are described as having, including, or comprising specific components, or where methods are described as having, including, or comprising specific steps, it is contemplated that, additionally, there are systems, apparatuses or compositions of the present invention that consist essentially of, or consist of, the recited components, and that there are methods according to the present invention that consist essentially of, or consist of, the recited processing steps.

It should be understood that the order of steps or order for performing certain action is immaterial as long as the invention remains operable. Moreover, two or more steps or actions may be conducted simultaneously.

The following description is for illustration and exemplification of the disclosure only, and is not intended to limit the invention to the specific embodiments described.

The mention herein of any publication, for example, in the Background section, is not an admission that the publication serves as prior art with respect to any of the present claims. The Background section is presented for purposes of clarity and is not meant as a description of prior art with respect to any claim.

BRIEF DESCRIPTION OF THE DRAWINGS

A full and enabling disclosure of the present disclosed embodiments, including the best mode thereof, directed to one of ordinary skill in the art, is set forth in the specification, which refers to the appended figures, in which:

FIG. 28 illustrates a schematic of an electrical current versus volume of blood characteristic, according to aspects of the present embodiments;

FIG. 29 illustrates a schematic of volume of air versus pressure of air characteristic, according to aspects of the present embodiments;

FIG. 30 illustrates a schematic of volume of blood versus pressure of blood characteristic, according to aspects of the present embodiments;

FIG. 31 illustrates a schematic of volume of air versus pressure of air characteristic, according to aspects of the present embodiments;

Figure 1:
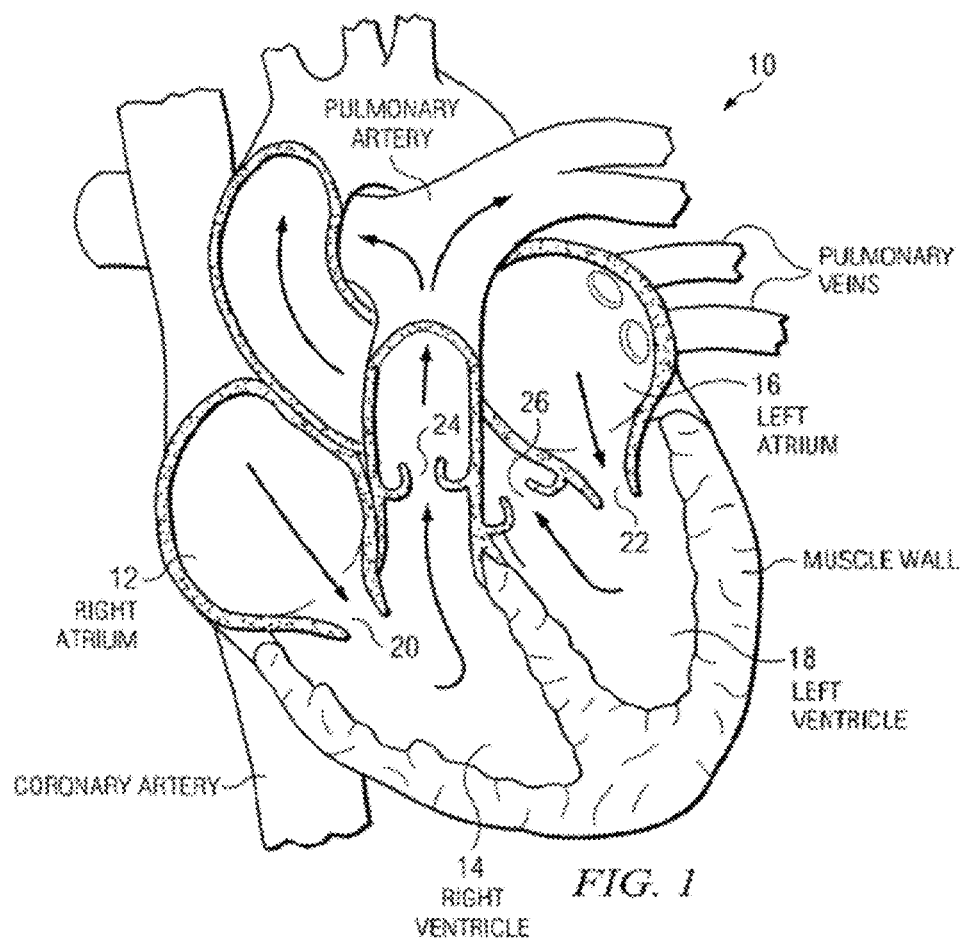
FIG. 1 illustrates a cross-sectional front view of a human heart.

Reference will now be made in detail to the present disclosed embodiments, one or more examples of which are illustrated in the accompanying drawings. The detailed description uses numerical and/or letter designations to refer to features in the drawings. Like or similar designations in the drawings and description have been used to refer to like or similar parts of the present embodiments.

Total Artificial Heart System

Figure 2:
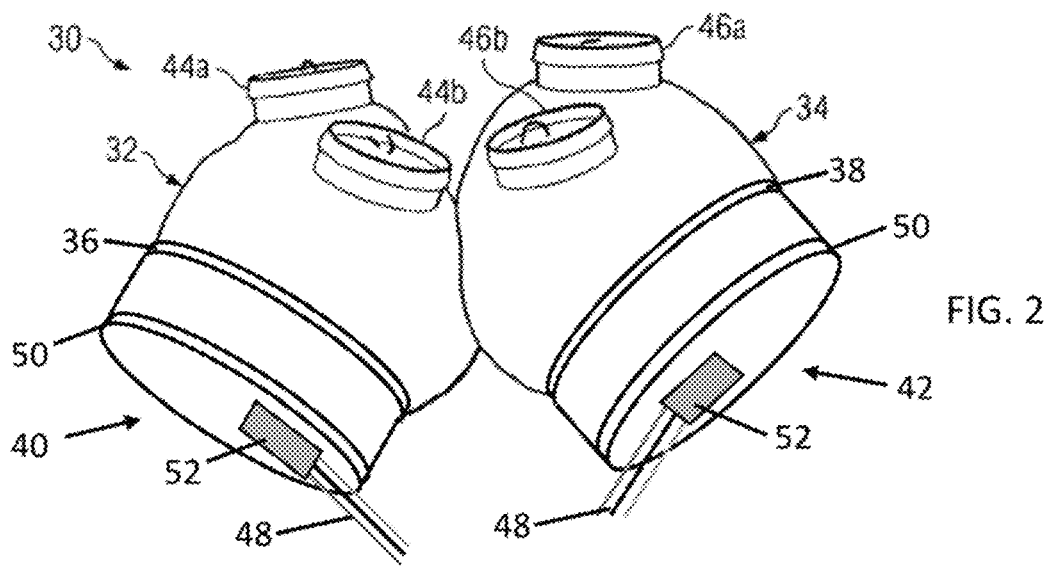
FIG. 2 illustrates a front view of a total artificial heart, according to aspects of the present embodiments.

Designed to operate much the same way as a human heart, the total artificial heart of the present disclosed embodiments replaces the two active chambers (i.e., the ventricles) of the human heart with corresponding artificial components. As illustrated in FIG. 2, such artificial heart 30 includes two separate chambers or ventricles 32, 34 that replace the right and left ventricles of the human heart, respectively. Each chamber 32, 34 is equipped with a respective diaphragm (36 and 38 in the right and left chamber, respectively) that has an air contact side and a blood contact side. Each diaphragm 36, 38 is designed as a spherical hemisphere. The total artificial heart 30 is implanted by connecting the top of the right chamber 32 to the right atrium 12 and the top of the left chamber 34 to the left atrium 16. The bottom of each chamber is provided with a drive system (40 and 42 in the right and left chambers, respectively) that is embedded in the patient's body, each drive system including electrical wires 48 extending out of the patient's body. Each drive system 40, 42 uses air to push against the respective artificial left and right ventricles 32, 34 via the respective diaphragm 36, 38, which discharges blood from the respective chamber 32, 34, thereby simulating and performing the function of a ventricle. As such, each diaphragm 36, 38 defines a transition or boundary between the ventricles 32, 34 and the drive systems 40, 42. The drive systems 40, 42 may each include a base 50, as well as one or more ports 52 for allowing the wires 48 to pass through to the base to the interior of the drive systems 40, 42. The total artificial heart 30 may also include artificial valves 44a (tricuspid), 46a (bicuspid), 44b (pulmonary), and 46b (aortic), which control the flow of blood from the respective atrium into each artificial ventricle 32, 34, and out to the circulatory systems, respectively.

Figure 3:
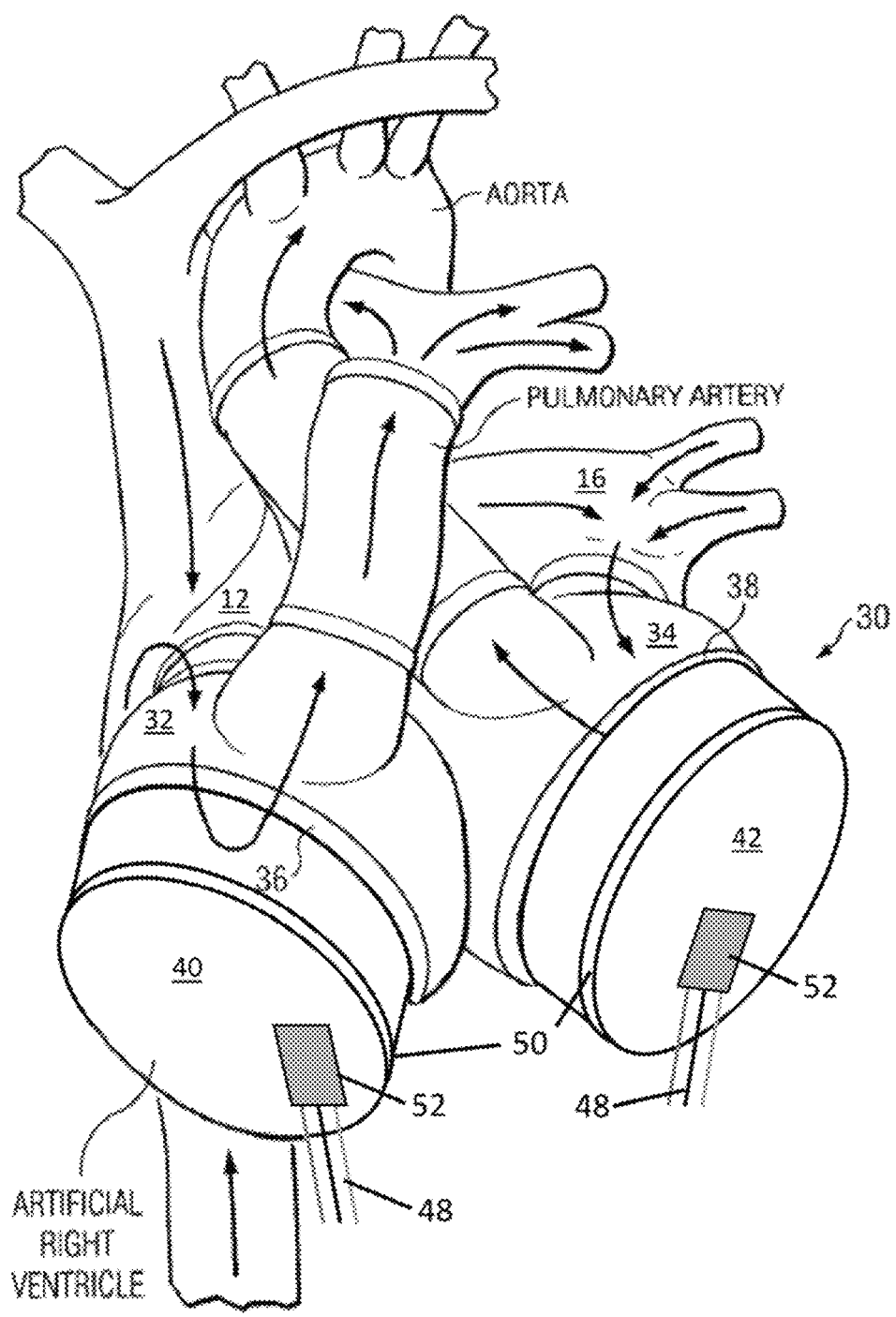
FIG. 3 illustrates a front view of an implanted total artificial heart, according to aspects of the present embodiments.

FIG. 3 illustrates a perspective view of an implanted artificial heart 30 connecting the top of the right chamber 32 to the right atrium 12 and the top of the left chamber 34 to the left atrium 16. The bottom of each chamber is provided with a drive system (40 and 42 in the right and left chamber, respectively) that is embedded in the patient's body and includes electrical wires that extend out of the patient's body, providing each drive system with electrical power. As each drive system 40, 42 uses air to push against the respective artificial left and right ventricles 32, 34 via the respective diaphragm 36, 38, blood is discharged from each chamber 32, 34, thereby pumping blood out of the heart during a systole or ejection phase. When the pressurized air is removed from the diaphragm, known as diastole or the filling phase, blood can enter the ventricle from the connected atrium. The rate at which blood enters the ventricle depends on the difference between the atrial pressure and the pressure on the air-side of the diaphragm. To increase this filling rate, a slight vacuum of about 10 mmHg on average may be established within the drive system 40, 42 on the air-side of the diaphragm 36, 38 during diastole. The pressure is higher during systole.

Figure 4:
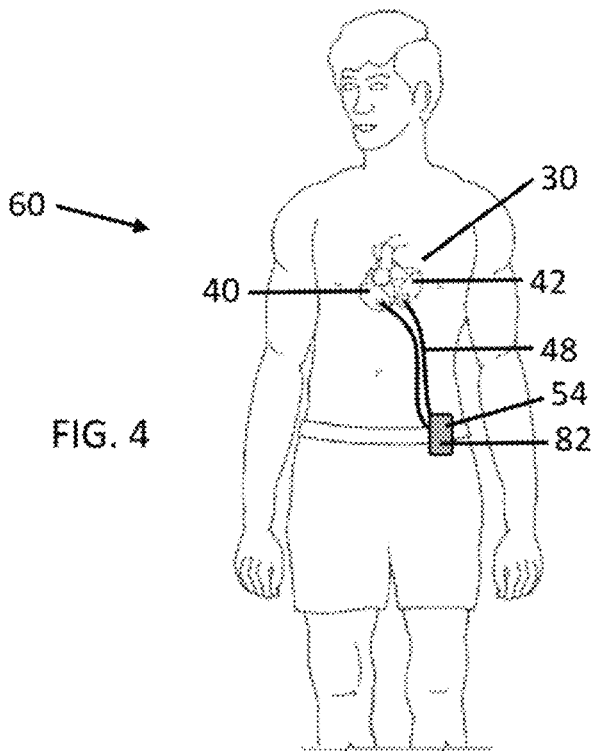
FIG. 4 illustrates a front view of an implanted total artificial heart system, according to aspects of the present embodiments.

FIG. 4 illustrates a front view of a total artificial heart system 60 according to aspects of the present embodiments. The total artificial heart system 60 may include the total artificial heart 30 including right and left drive systems 40, 42 implanted within the chest cavity of a patient. Each drive system 40, 42 may be connected to a mobile power supply 54 via one or more wires 48. The mobile power supply 54 may include a local interface (not shown) for controlling the function of the total artificial heart system 60, as well as battery ports and local control buttons. In operation, the local power supply 54 may be worn on a belt or strapped around the chest, shoulder, or waist, or carried in a pocket, such that the patient may move about freely without having to carry a mobile compression unit within one or both hands. In addition, the overall weight of the mobile power supply 54 may be less than about three (3) pounds, or from about two (2) pounds to about three (3) pounds, or from about one (1) pound to about two (2) pounds, or less than about one (1) pound. In other embodiments, the overall weight of the mobile power supply 54 may be from about four (4) ounces to about sixteen (16) ounces, or from about six (6) ounces to about fourteen (14) ounces, or from about eight (8) ounces to about twelve (12) ounces.

Drive System

Figure 5:
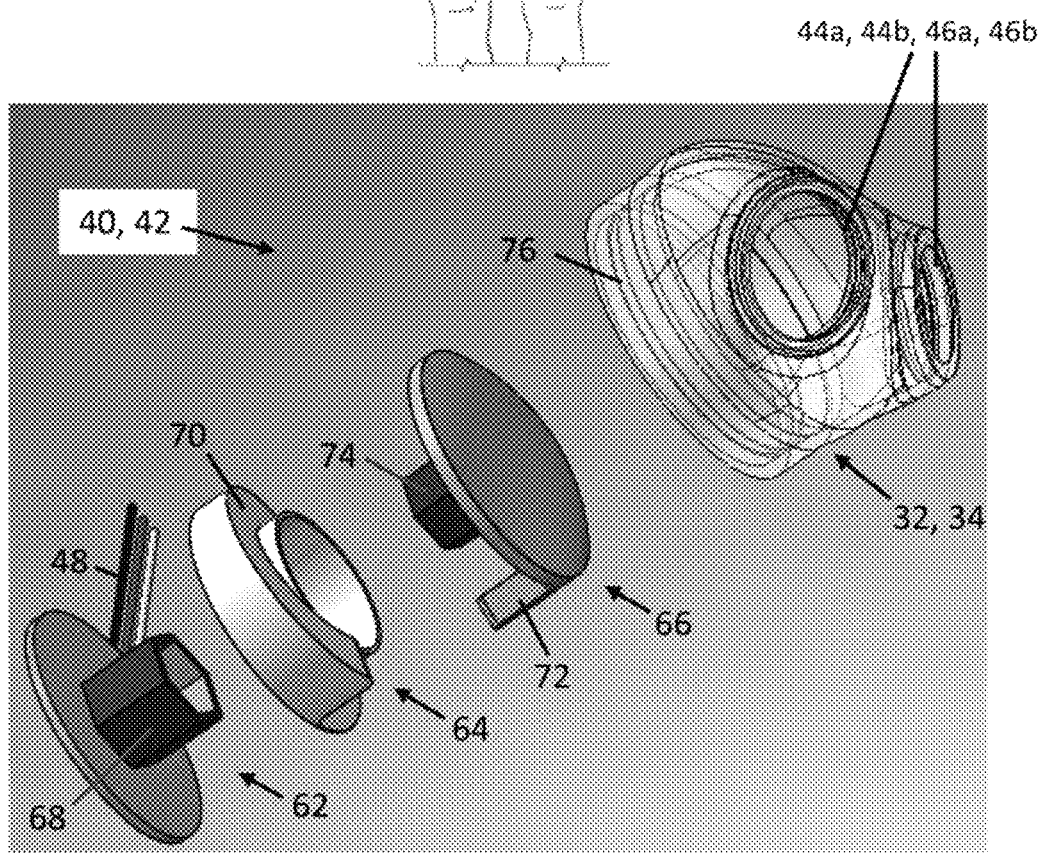
FIG. 5 illustrates a perspective view of a total artificial heart drive system, according to aspects of the present embodiments.

FIG. 5 illustrates a perspective view of a disassembled arrangement of components within each drive system 40, 42 of the total artificial heart system 60, according to aspects of the present disclosed embodiments. The drive system 40, 42 may be coupled to the right and left artificial ventricles 32, 34, and may include a drive system stator assembly 62, a drive system rotorcam 64, and a drive system cam follower 66. The stator assembly 62 may be electrically coupled to the wires 48 such that electrical power is supplied to the stator assembly 62, which also acts as a base of an electric motor (for example a brushless director current (BLDC) motor). The rotorcam 64 may slide onto the stator assembly 62 around a hexagonal housing 68. The rotorcam 64 acts both as a rotor as part of the electric motor, as well as a cam as part of a cam and follower system. As such, the rotorcam 64 may include one or more permanent magnets, or may be composed of a solitary permanent magnetic material. In addition, the rotorcam 64 may include at least one ramp 70 for use in the cam and follower system. The follower 66 may include at least one tooth 72 for interfacing with the ramp of the rotorcam 64. The follower 66 may also include one or more hexagonal shafts 74 for sliding into the one or more hexagonal bases 68, thereby preventing the follower 66 from rotating, but allowing it to slide up and down within the drive system 40, 42. Each right and left artificial ventricle 32, 34 may include a lower housing 76 which may extend around the drive system assembly, allowing for movement of the rotorcam 64 and follower 66 therewithin.

In operation, electrical charge runs from the wires 48 into the base 68 and eventually through one or more motor windings 130 (shown in FIGS. 16-18) thereby creating an electromagnetic force causing the rotorcam 64 to rotate (i.e., due to the permanent magnet). A cylindrical housing 128 (shown in FIGS. 16-18) extending from the stator assembly 62 may surround both the hexagonal housing 68 as well as the motor windings 130 (shown in FIGS. 16-18), and may be disposed radially within an inner bore 78 of the rotorcam 64, thereby providing a bearing (for example a sleeve bearing) about which the rotorcam 64 may rotate. As the rotorcam 64 rotates, the tooth 72 interfaces with the ramp 70, thereby causing the follower 66 to rise and fall with the changing height (i.e., incline) of the ramp 70. A spring 134 (shown in FIG. 17) disposed within the hexagonal shaft 74, and coupling the follower 66 to the stator assembly 62 holds the follower 66 against the stator assembly 62, even as the ramp 70 pushes the follower 66 away from the stator assembly 62 (i.e., via the tooth 72). As the follower 66 moves up and down as a result of the movement of the rotorcam 64 and tooth 72, the volume within each drive system 40, 42 as well as within the right and left ventricles 32, 34 increases and decreases, thereby simulating the contraction and expansion of a human heart and allowing blood to flow into, and then be pumped out of, the total artificial heart 30. Internal air pressure within the drive system 40, 42 may also act as a spring, by helping to suction the cam follower 66 back toward the base 50 after the drop-off 88 (shown in FIG. 7) has passed under the tooth 72.

Figure 6:
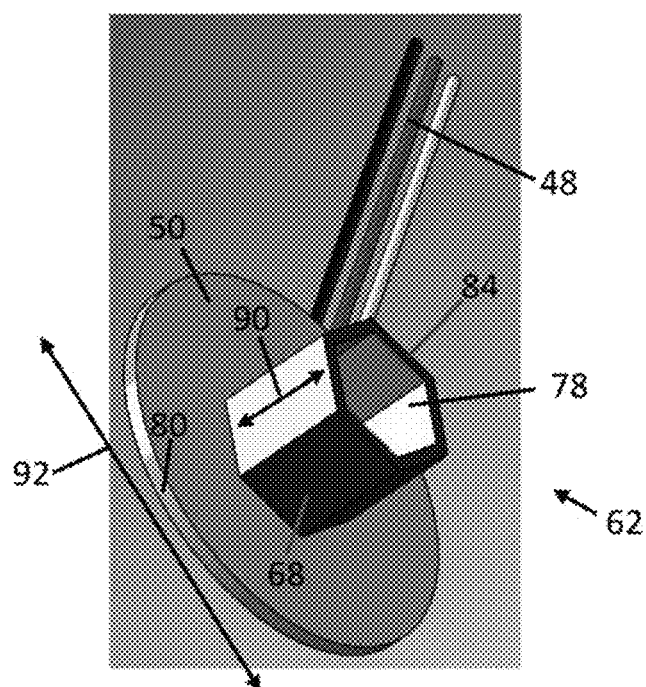
FIG. 6 illustrates a perspective view of a drive system stator assembly base, according to aspects of the present embodiments.
Figure 16:
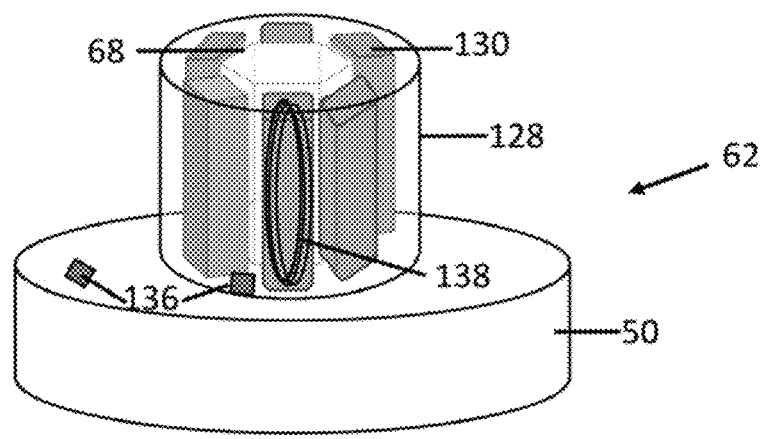
FIG. 16 illustrates a perspective view of a drive system stator assembly, according to aspects of the present embodiments.
Figure 17:
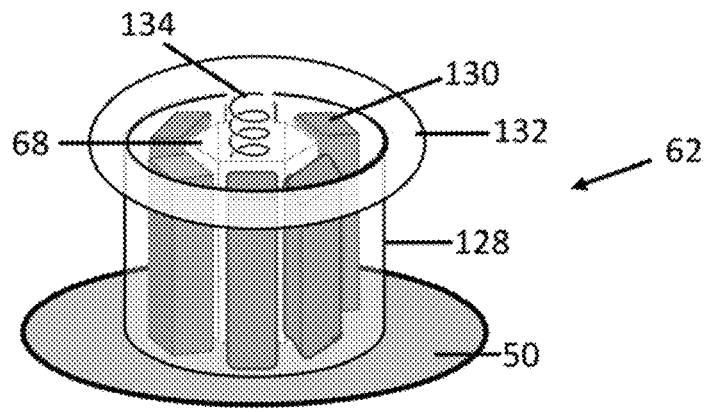
FIG. 17 illustrates a perspective view of a drive system stator assembly, according to aspects of the present embodiments.
Figure 18:
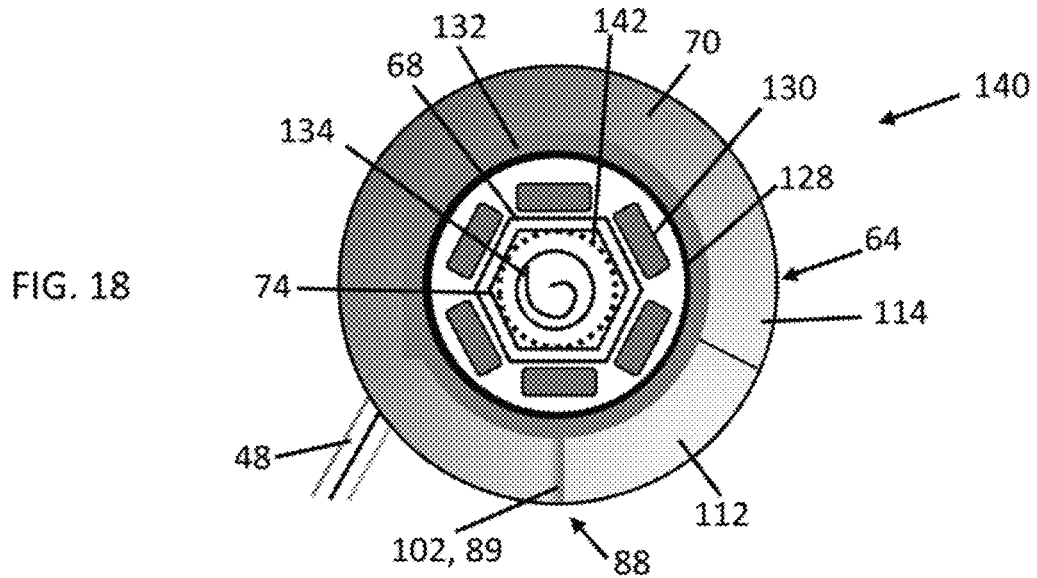
FIG. 18 illustrates a top view of a drive system stator assembly, according to aspects of the present embodiments.

FIG. 6 illustrates a perspective view of the stator assembly 62 including one or more electrical wires 48 coupled to a base portion 50 from which the hexagonal housing 68 extends. The hexagonal housing 68 may include a hexagonal cross-section. In other embodiments, the housing 68 may include a square-shaped, rectangular, triangular, elliptical, pentagonal, or other shaped cross-section such that it allows the hexagonal (or other-shaped) shaft 74 (shown in FIG. 5) of the follower 66 to slide therewithin, without rotating. An interior 78 of the hexagonal housing 68 is sized and shaped such that the internal geometry matches that of the hexagonal shaft 74 (albeit slightly larger to allow for tolerances between components). FIG. 6 also illustrates a height 90 of the hexagonal housing 68, as well as a diameter 92 of the base portion 50. In one or more embodiments, the diameter 92 of the base portion 50 may be from about two (2) to about four (4) times the height 90 of the hexagonal housing 68. In another embodiment, the diameter 92 of the base portion 50 may be from about 2.5 to about 3.5 times the height 90 of the hexagonal housing 68. In another embodiment, the diameter 92 of the base portion 50 may be about three (3) times the height 90 of the hexagonal housing 68. The hexagonal housing 68 may include a wall thickness 84 from about 0.5 millimeters to about five (5) millimeters, or from about 0.8 millimeters to about three (3) millimeters, or from about one (1) millimeter to about two (2) millimeters. The stator assembly 62 may also include an outer lip 80 extending around the outer diameter of the base portion 50. The outer lip 80 may interface with the lower housing 76 (shown in FIG. 5) of the right or left artificial ventricle 32, 34 such that the lower housing 76 extends tightly around the outer lip 80 in a compression fit. The lower housing 76 may also include one or more notches, grooves, slots, slits, and/or other features for holding the outer lip 80 thereby tightly scaling the left and right drive system assemblies 40, 42. In operation, neither the lower housing 76 nor the outer lip 80 rotates. As such, in some embodiments, the lower housing 76 and the outer lip 80 may be epoxied, welded, brazed, soldered, glued, adhered, bonded, taped, fused, sintered, and/or otherwise joined to one another. Other aspects of the stator assembly 62 and motor architecture are illustrated in FIGS. 16-18.

Figure 7:
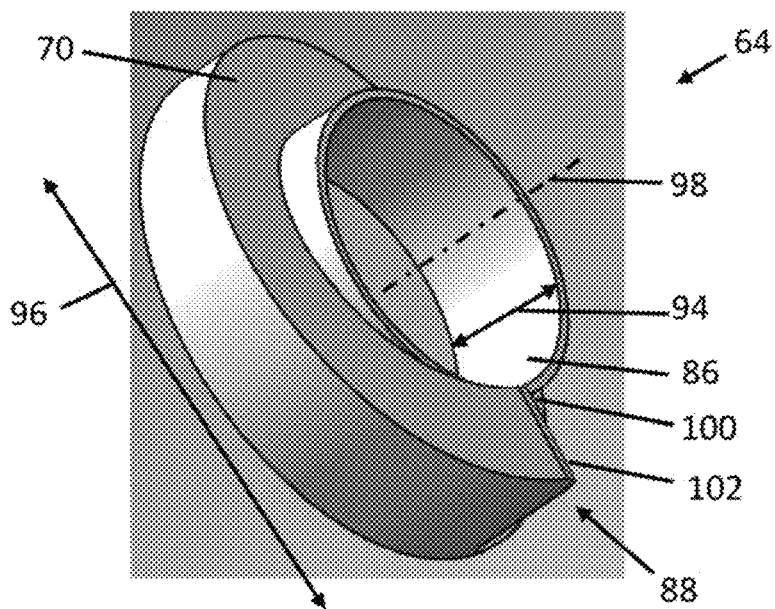
FIG. 7 illustrates a perspective view of a drive system rotorcam, according to aspects of the present embodiments.

FIG. 7 illustrates a perspective view of the rotorcam 64 including the ramp 70 which may extend circumferentially around the rotorcam 64, radially outward of a center bore 86. The center bore 86 may include a hollow, cylindrical space having a height 94 and being concentric about a rotorcam centerline 98. The ramp 70 gradually increases in height until it reaches the full height 94 of the rotorcam 64, at which point the ramp 70 interfaces with a drop-off 88, which itself interfaces with a bottom portion 100 (also illustrated in FIGS. 9-11) of the ramp 70. The rotorcam 64 may also include a rounded transition 102 between the top of the drop-off 88 and the bottom portion 100. In one embodiment, a diameter 96 of the rotorcam may be from about two (2) to about ten (10) times the rotorcam height 94. In another embodiment, the diameter 96 may be from about three (3) to about eight (8) times the rotorcam height 94. In another embodiment, the diameter 96 may be from about four (4) to about seven (7) times the rotorcam height 94. In another embodiment, the diameter 96 may be from about five (5) to about six (6) times the rotorcam height 94. The rotorcam 64 may act as a permanent magnet and may be composed of neodymium iron boron (ND-Fe—B), iron, cobalt, samarium cobalt (SM-Co), aluminum, alnico, bonded Nd—Fe—B, magnetite, ceramic (hard ferrite), ferrite, gadolinium, rare earth elements, strontium, barium, iron (III) oxide, combinations and alloys thereof, and other magnetic materials. By integrating a rotor for use in an electric motor with a cam, the rotorcam 64 achieves two functions simultaneously, while also reducing the overall volume of the drive system 40, 42, and the number of individual parts.

Figure 8:
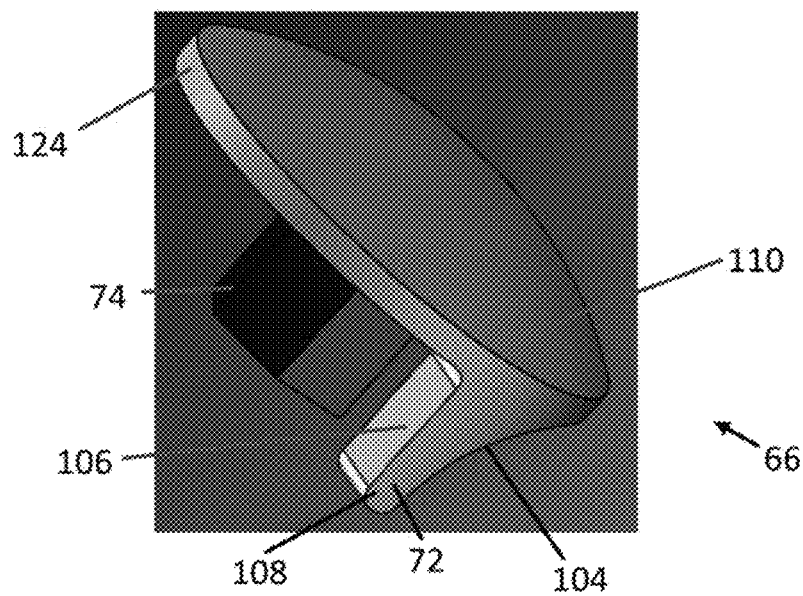
FIG. 8 illustrates a perspective view of a drive system cam follower, according to aspects of the present embodiments.

FIG. 8 illustrates a perspective view of a cam follower 66 including the tooth 72 and hexagonal shaft 74. The hexagonal shaft 74, in other embodiments, may include other-shaped cross-sections, including but not limited to square-shaped, rectangular, triangular, elliptical, pentagonal, and/or other-shaped cross-sections such that the shaft 74 may slide within the housing 68, without rotating. The tooth 72 may include a rounded taper 104 along a leading edge along as well as a substantially linear (or planar) portion 106 along a trailing edge. The linear portion 106 allows the tooth 72 (and cam follower 66) to drop down toward the base portion 50 (shown in FIG. 6), after the drop-off 88 (shown in FIGS. 7 and 9-11) passes underneath the tooth 72. The rounded taper 104 along the leading edge of the tooth 72 increases the effective cross-sectional area of the tooth 72, thereby increasing the strength and robustness of the tooth 72, and reducing the likelihood it will become damaged or broken. The tooth 72 may also include a rounded tip 108, which may aid in preventing damage to the tooth 72 and/or other components of the drive system 40, 42.

Referring still to FIG. 8, the cam follower 66 may also include a follower dome 110 which may include a domed curvature and/or gradual contouring (i.e., a larger diameter contouring than the diameter of the cam follower 66). The follower dome 110 may be convex toward the left and/or right artificial ventricle 32, 34 (i.e., upwardly convex), and may form both a barrier and interface between the blood side of the follower dome 110 and the air side of the follower dome 110. At an outer diameter, the carrier dome 110 interfaces with an outer rim 124, which may fit within the cylindrical housing 76. Via the follower dome 110, pressure may be exchanged between the blood and the air while the follower dome 110 simultaneously acts as a barrier between the two fluids, thereby preventing the blood from ever being exposed to the air, and vice versa. As the follower dome 110 (i.e., and cam follower 66) moves up and down, the volume of the air within each drive system 40, 42 as well as the volume of blood within the right and left ventricles 32, 34 continuously changes. In other embodiments, the cam follower 66 of FIG. 8 may include multiple teeth 72, circumferentially spaced around the cam follower 66 while the rotorcam 64 of FIG. 7 may include multiple ramps circumferentially spaced around the rotorcam 64, and corresponding to the spacing and number of teeth 72 of the cam follower 66. Each of the cam follower 66, the rotorcam 64, and the stator assembly 62 may have about the same outer diameter. In one or more embodiments, each of the cam follower 66 and the rotorcam 64 may include a slightly smaller outer diameter than the stator assembly 62 due to the cam follower 66 needing to translate up and down within the lower housing 76, and due to the rotorcam 64 needing to rotate within the lower housing 76. The base portion 50 may fit tightly within the lower housing 76 as it neither rotates nor translates within the lower housing 76, and thus does not need to move relative to the lower housing 76.

Figure 9:
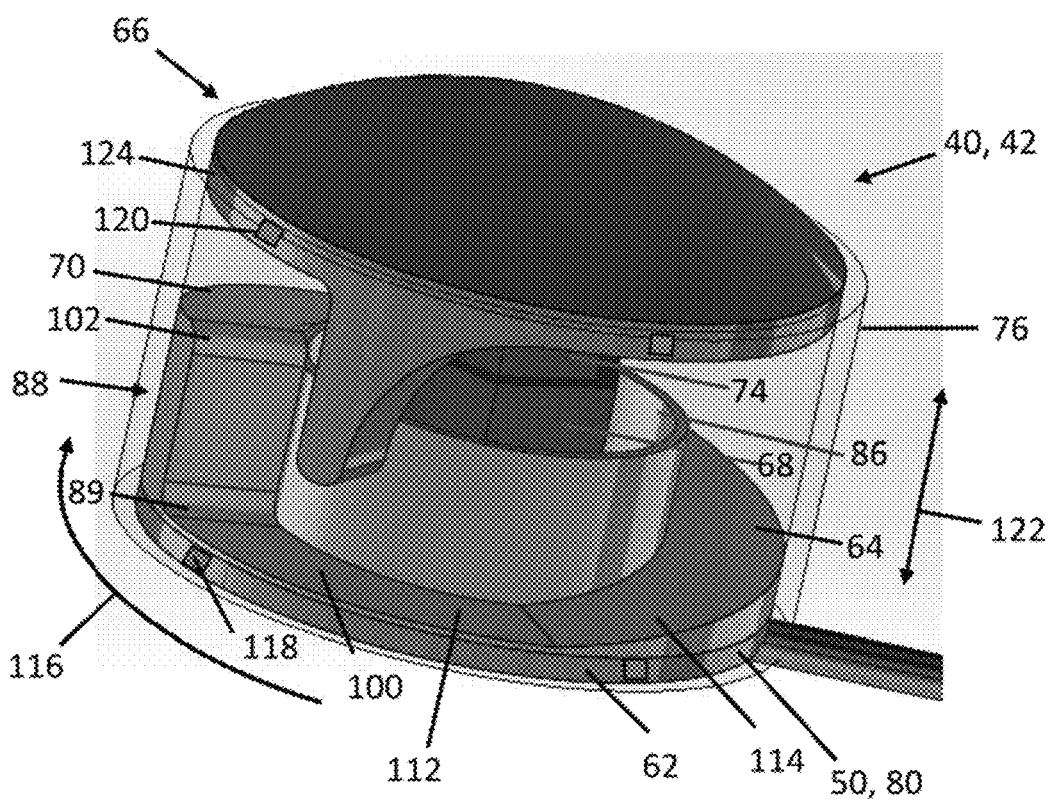
FIG. 9 illustrates a perspective view of an assembled drive system, according to aspects of the present embodiments.

FIG. 9 illustrates an assembled perspective view of the drive system 40, 42 including the stator assembly 62, the rotorcam 64, and the cam follower 66. A clockwise direction 116 (i.e., when viewed from above) indicates the direction in which the rotorcam 64 rotates in the embodiment of FIG. 9. An axial or longitudinal direction 122 (i.e., parallel with the cam centerline 98, shown in FIG. 7) indicates the direction in which the cam follower 66 translates in the embodiment of FIG. 9. The drive system 40, 42 may include a rounded portion 102 defining a transition between the top of the ramp 70 and the drop-off 88, as well as a bottom rounded portion 89 defining a transition between the drop-off 88 and the bottom portion 100. The bottom portion 100 may include a flat portion 112 that transitions into an inclined portion 114. In other embodiments, the bottom portion 100 may include only an inclined portion 114 (i.e., the ramp 70) such that the bottom rounded portion 89 forms a transition between the drop-off 88 and the inclined portion 114 (i.e., without first transitioning to a flat portion 112). The hexagonal shaft 74, in the embodiment of FIG. 9, is partially disposed within the hexagonal housing 68, both being disposed radially within the center bore 86 of the rotorcam 64. Each of the stator assembly 62, the rotorcam 64, and the cam follower 66 may be disposed within the lower housing 76 (i.e., extending down from the left and/or right ventricle 32, 34 (not shown)) or within an alternate cylindrical housing 76. In the embodiment of FIG. 9, the drive system 40, 42 may also include at least one first proximity sensor 118 disposed within the base portion 50 (or outer lip 80) of the stator 62, as well as at least one second proximity sensor 120 disposed within the cam follower 66. The first and second proximity sensors 118, 120 may be used to determine the distance between the base portion 50 and an outer rim 124 of the cam follower 66. This distance is directly proportional to the volume of air within each drive system 40, 42, which in turn is inversely proportional to the volume of blood within the right and/or left ventricle 32, 34, at any given instant. By sensing and tracking the volume of blood being pumped through the total artificial heart system 30 via the first and second proximity probes 118, 120, a total cardiac output or production may be approximated and monitored.

Figure 10:
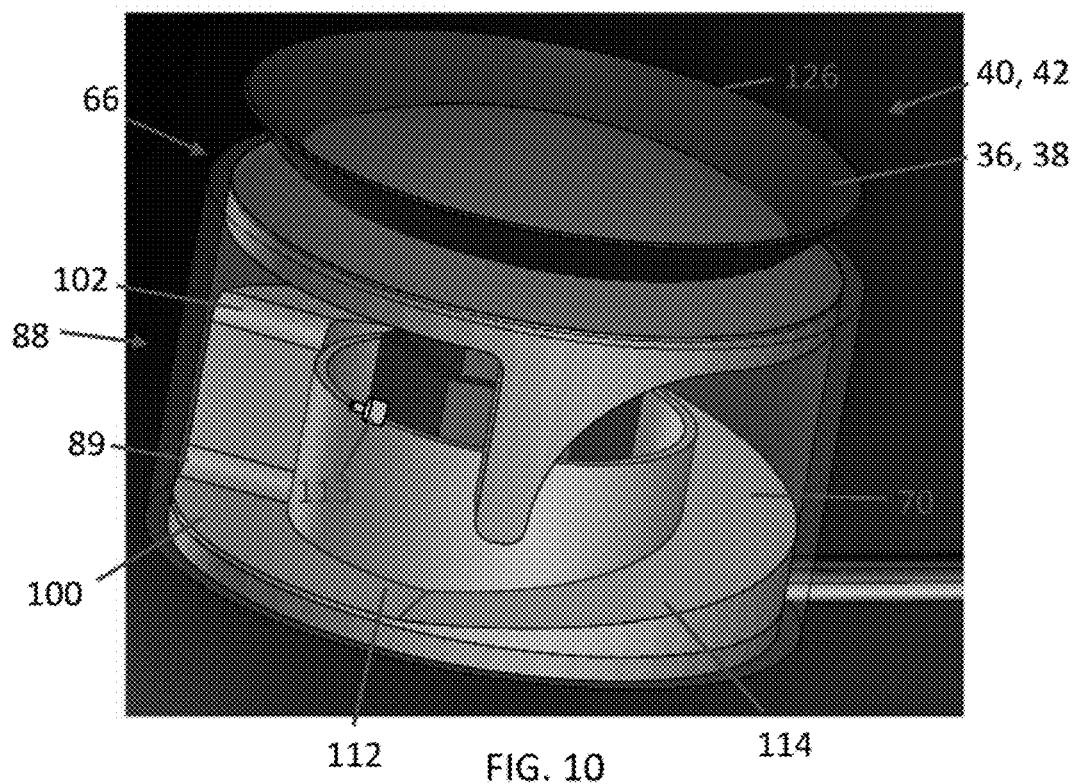
FIG. 10 illustrates a perspective view of an assembled drive system, according to aspects of the present embodiments.

FIG. 10 illustrates an assembled perspective view of the drive system 40, 42 including the stator assembly 62, the rotorcam 64, and the cam follower 66. The cam follower 66 may include the rounded portion 102 at the top of the ramp 70 transitioning to the drop-off 88, which transitions to the bottom rounded portion 89, and then to the bottom portion 100 which comprises the flat portion 112, and the inclined portion 114 (or ramp 70). In the embodiment of FIG. 10, the diaphragm 36, 38 extends from the follower dome 110. The diaphragm 36, 38 may extend both axially upward as well as radially outwardly from the follower dome 110 such that a diaphragm leading edge 126 may make contact with the right or left ventricle 32, 34, thereby providing an extra barrier or seal between the blood chambers (i.e., ventricles 32, 34) and air chambers (i.e., the drive systems 40, 42) of the total artificial heart 30. The drive system 40, 42 may include one or more pressure sensors 113 disposed on the rotorcam 64 and/or on the stator assembly 62 (for example on the retaining lip 132 of FIG. 17, and/or within the cylindrical housing 128 or stator base portion 50). The one or more pressure sensors 113 may be used to determine the pressure of the air within the drive system 40, 42 as the cam follower 66 rises and falls due to the rotation of the rotorcam 64.

Figure 11:
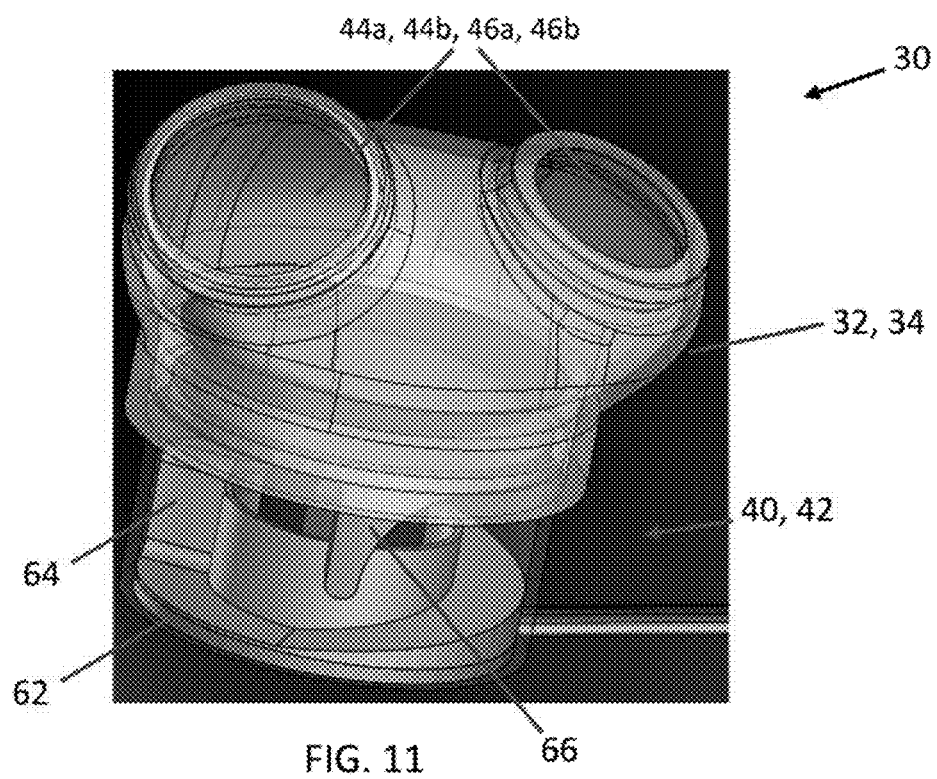
FIG. 11 illustrates a perspective view of an assembled drive system, according to aspects of the present embodiments.

FIG. 11 illustrates an assembled perspective view of the total artificial heart 30 with the right and/or left ventricle 32, 34 coupled to the drive system assembly 40, 42 including the stator assembly 62, the rotor cam 64, and the cam follower 66. FIG. 11 also illustrates the locations of one or more artificial valves including the tricuspid 44*a*, the bicuspid 46*a*, the pulmonary 44*b*, and the aortic 46*b*. In each of the embodiments of FIGS. 9-11, the one or more teeth 72 of the cam follower 66 would generally be in contact with the one or more ramps 70 of the rotorcam 64 while the drive system 40, 42 is in operation.

Figure 12:
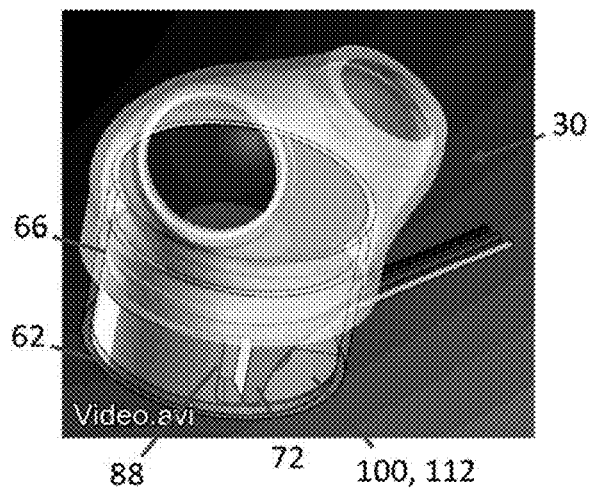
FIG. 12 illustrates a perspective view of an assembled drive system, according to aspects of the present embodiments.
Figure 13:
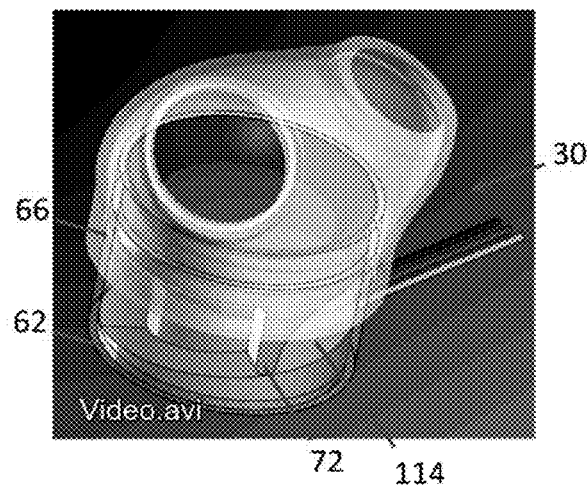
FIG. 13 illustrates a perspective view of an assembled drive system, according to aspects of the present embodiments.
Figure 14:
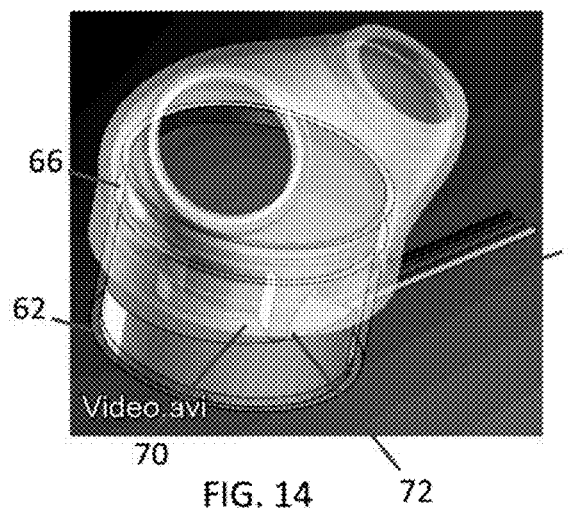
FIG. 14 illustrates a perspective view of an assembled drive system, according to aspects of the present embodiments.
Figure 15:
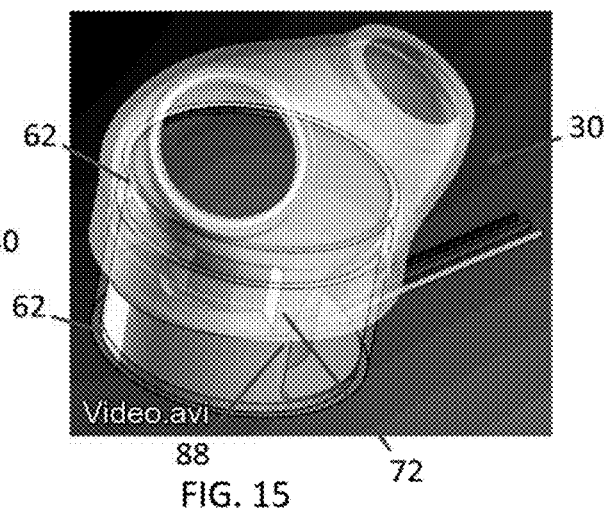
FIG. 15 illustrates a perspective view of an assembled drive system, according to aspects of the present embodiments.

FIGS. 12-15 show progressive perspective views of the total artificial heart 30 in operation, according to aspects of the present embodiments. In the embodiment of FIG. 12, the at least one tooth 72 is at the flat portion 112 of the bottom portion 100 at the bottom of the drop-off 88. In the embodiment of FIG. 13, the at least one tooth 72 is on the inclined portion 114 (or ramp 70). In the embodiment of FIG. 14, the at least one tooth 72 is close to the top of the ramp 70. In the embodiment of FIG. 15, the at least one tooth 72 is at the very top of the ramp 70, at the edge of the drop-off 88. In the embodiments of FIGS. 12-15, the cam follower 66 gets progressively further away from the stator assembly 62, which corresponds to blood being pushed by the cam follower 66 (and diaphragm 36, 38) out of the right or left ventricle 32, 34. The cam follower 66 does not rotate with the rotorcam because the hexagonal housing 68 does not permit the hexagonal shaft 74 to rotate therewithin. The housing 68 and shaft 74 may similarly be square-shaped, triangular, and other shapes (i.e., other than circular) such that the housing 68 will hold the shaft 74 but prevent it from rotating with the rotorcam 64.

In operation, the right and left ventricles 32, 34 are only partially filled during normal conditions, in order to provide extra capacity when the blood flow in the body of the patient is increased as a result of physical activity. In one embodiment, the air side of each ventricle has a volume of approximately from about three (3) to about six (6) cubic inches, or from about four (4) to about five (5) cubic inches, or from about 4.1 to about 4.7 cubic inches). Each of the diaphragms 36, 38 may have an area from about four (4) to about eight (8) square inches, or from about five (5) to about seven (7) square inches, or from about 5.7 to about 6.6 square inches. The compression ratios of each drive system 40, 42 on the air side (i.e., ratio of maximum volume to minimum volume for a given operating condition) varies from one operating mode to the next. For example, in a maximum blood volume case (i.e., strenuous exercise), the compression ratio may be about three (3) to one (1), or from about 2.5 to about 3.5 to one (1). In a moderate exercise or activity case, the compression ratio may be about to (2) to one (1), or from about 1.75 to about to 2.5 to one (1). In a resting or sleeping mode of operation, the compression ratio may be about 1.5 to one (1) or from about 1.25 to about 1.75 to one (1).

Each of the components of the drive system 40, 42 including the stator assembly 62, the rotorcam 64, the cam follower 66, the wires 48, as well as the right and left artificial ventricles 32, 34 may be coated with an inert material that does not cause a reaction or response within the human body. In one embodiment, each of the components of the drive system 40, 42 may be coated with a segmented polyurethane solution (SPUS) that is both biocompatible (or bio-inert) within the human body (i.e., completely inert), and that is also both fatigue and strain resistant. In one or more embodiments, right and left artificial ventricles 32, 34 may be composed of SPUS. The SPUS components may be formed via one or more molding processes as separate components and then subsequently glued together. In other embodiments, various components or subcomponents may be formed of SPUS via a single injection-molding process. One or more components and/or sub-components of the present disclosed embodiments may also be composed of or coated with other synthetic materials, such as silicone rubber, thermoplastic elastomers (TPE), and/or polyvinyl chloride (PVC). The SPUS material used in connection with the present disclosed embodiments may be able to accommodate tensile loads from about 5000 psi to about 8000 psi, and may be able to accommodate stiffness (i.e., modulus) loadings from about 400 psi to about 800 psi or from about 450 psi to about 750 psi. By using SPUS materials (either as the underlying component materials or as coatings on components that are composed of other materials) in connection with the components of the present disclosed embodiments, reactions and other responses occurring from exposure of one or more biological tissues to the components described herein may be avoided.

BLDC Motor Architecture

FIGS. 16-18 illustrate embodiments of the stator assembly 62 (FIGS. 16 and 17) and an electric motor assembly 140 (FIG. 18), according to aspects of the present embodiments. Referring to FIG. 16, the stator assembly 62 may include a plurality of winding groups 130 each oriented longitudinally and spaced around the hexagonal housing 68. Each of the winding groups 130 may include longitudinally aligned conductive coil wires 138 wound around one or more cores (not shown; i.e., solid frames, supports, and/or features that provide a structure around which the wires 138 may be wound). In the embodiment of FIG. 16, six (6) stator winding groups 130 are included, but electric motors according to the present embodiments (including brushless direct current (BLDC) motors) may include other numbers of windings including, for example, eight, (8), nine (9), twelve (12), twenty-four (24), forty-eight (48), as well as other numbers of stator windings 130. Each of the stator winding groups 130 may be composed of silicon core iron, copper, aluminum, and other materials. Opposing winding groups 130 (for example, the first and fourth, the second and fifth, and the third and sixth winding groups 30 in the embodiment of FIG. 16) may be electrically coupled such that they provide opposing polarity (i.e., north or south) to the surrounding rotorcam 64 (not shown). Adjacent sets of opposing windings 130 may then be electrically activated in succession such that each set imparts an electromagnetic force on the rotorcam 64, causing it to rotate about the stator assembly 62.

Referring still to FIG. 16, the stator assembly 62, may also include a thicker base 50 to accommodate an integral battery system, motor controls and/or circuitry, as well as other components. The stator assembly 62 may also include one or more Hall effect devices or Hall sensors 136 disposed within the base 50 or radially within the cylindrical housing 128. The one or more Hall sensors 136 may be used to sense the presence of a strong and/or changing electromagnetic field (i.e., from the rotorcam 64 as it rotates past), in order to determine the rotational position of the rotorcam 64 (and thus the rotational speed as well). The Hall sensors 136 may also be used to control the rotational speed of the rotorcam 64 (i.e., overall revolutions per minute or radians per second, for example), as well as the instantaneous angular speed within each revolution, which also may be selectively controlled.

FIG. 17 illustrates a perspective view of the stator assembly 62 according to aspects of the present embodiments. The stator assembly 62 may include one or more springs 134 disposed within the hexagonal housing 68. The spring may be coupled to both the stator base 50, as well as the cam follower 66 (shown in FIGS. 5 and 8-15) for pulling the cam follower 66 back toward the stator base 50 when the one or more teeth 72 (shown in FIGS. 5 and 8-15) passes the dropoff 88 (shown in FIGS. 5 and 8-15). Stated otherwise, one end of each spring 134 is coupled to the bottom of the hexagonal housing 68 while the other end of each spring 134 is coupled to the top of the hexagonal shaft 74. The one or more springs 134 are disposed within both the hexagonal housing 68 and the hexagonal shaft 74. The spring 134 expands as the rotorcam 64 pushes the tooth 72 and cam follower 66 upward. The one or more springs 134 then pull the cam follower 66 back toward the stator assembly 62 after the drop-off 88 passes under the tooth 72.

Referring still to FIG. 17, the stator assembly 62 may also include a retaining lip 132 extending radially outwardly from the upper circumference of the cylindrical housing 128. The retaining lip 132 may be ring-shaped and may be concentric about the cylindrical housing 128. The retaining lip 132 may be used to hold the rotorcam 64 to the stator assembly 62, thereby allowing the rotorcam 64 to rotate about the cylindrical housing 128, while preventing the rotorcam 64 from translating upwardly and/or downwardly (i.e., along the longitudinal direction). In embodiments that do not include a retaining lip 132, the rotorcam 64 may remain biased against the stator base 50 via the one or more teeth 72 (shown in FIGS. 5 and 8-15), which is pulled downwardly via the one or more springs 134. Because the hexagonal housing 68 is radially disposed within the one or more winding groups 130, the hexagonal housing 68 may also be termed an inner stator housing 68. Similarly, because the cylindrical housing 128 is disposed radially outward of the one or more winding groups 130, the cylindrical housing 128 may also be termed an outer stator housing 128.

FIG. 18 illustrates a top view of a motor assembly 140 (for example, a BLDC motor assembly), according to aspects of the present embodiments. As illustrated in FIG. 18, the motor assembly 140 may include the rotorcam 64 disposed about the cylindrical housing 128, and longitudinally held in place via the retaining lip 132. The rotorcam 64 may include the ramp 70, which may include the rounded portions 102, 89 at the drop-off 88, as well as the flat portion 112, and the inclined portion 114. Disposed radially within the cylindrical housing 128, the motor assembly 140 may include multiple winding groups 130, the hexagonal housing 68, the hexagonal shaft 74, and the one or more springs 134. One or more wires 48 may also be electrically coupled to the motor assembly 140. In the embodiment of FIG. 18, the motor assembly 140 may include one or more dampers 142 disposed within the hexagonal housing 68 at the bottom of the hexagonal housing 68. The one or more dampers 142 may be compressible, and may extend up to only a fraction or partial length of the height 90 of the hexagonal housing 68. For example, the damper 142 may extend up to only about five (5) percent to about fifty (50) percent of the height 90 of the hexagonal housing 68. In other embodiments, the damper 142 may extend to from about ten (10) percent to about forty (40) percent of the height 90 of the hexagonal housing 68. In other embodiments, the damper 142 may extend to from about fifteen (15) percent to about thirty (30) percent of the height 90 of the hexagonal housing 68. In other embodiments, the damper 142 may extend to from about twenty (20) percent to about twenty-five (25) percent of the height 90 of the hexagonal housing 68.

Referring still to FIG. 18, in operation, the one or more dampers 142 prevents the cam follower 66 (and one or more teeth 72 thereof) from slamming too violently or rapidly back down onto the bottom portion 100 (for example onto the flat portion 112) of the rotorcam 64 (i.e., after the drop-off 88 passes under the one or more teeth 72). As such, the one or more dampers 142 may prevent wear and tear of the drive system 40, 42, and may also allow for a more gradual operation of the cam follower 66 within the right and/or left ventricle 32, 34. The central venous pressure helps fill the heart (with blood) each time the tooth 72 drops off the drop-off 88. The damper 142 helps prevent a high change in pressure too quickly and ensures a more gentle and gradual ramp drop-off. For example, by using the damper 142, pressure drops (i.e., dP/dT) above a certain threshold may be avoided. The motor 140 may also be used to prevent rapid changes in pressure. Because the motor 140 may be selectively controlled to any rotational speed (even within a single rotation), multiple rotational speeds may be chosen during each of the systole and diastole phases of each cycle. For example, during the systolic phase when the right and left ventricles 32, 34 are being evacuated, the motor 140 may be controlled such that the rotational speed is higher while the tooth or teeth 72 are on the inclined portion 114 of the ramp (thereby raising the cam follower 66 and contracting the ventricles 32, 34 quickly). The motor 140 may then be controlled to a slower speed for the beginning of the diastolic phase (when the ventricles 32, 34 are expanding and filling), allowing the tooth 72 and cam follower 66 to drop all the way back down to the flat portion 112. In one or more embodiments, the motor 140 may be controlled such that transitions between faster and slower rotational speeds are made gradually and/or gently so that the artificial valves 44a, 44b, 46a, 46b do not experience excessive stresses by opening or closing too quickly. By gradually transitioning between slower rotational speeds and faster rotational speeds (and vice versa), "water hammer" effects may be avoiding, thereby reducing potential damage to the artificial valves 44a, 44b, 46a, 46b themselves (i.e., by gently opening and closing them), but also reducing damage to the surrounding blood. In addition, fluid shear stress (i.e., within the blood) may be minimized by limiting the pressure drop (i.e., dP/dT) by controlling the rotational speed of the rotorcam 64.

In operation, anywhere from one (1) to five (5) or six (6) inch-pounds of torque may be required to rotate the drive system 40, 42, (the higher end of the torque range corresponding to a hypertensive patient whose blood pressure will externally act on the drive system 40, 42, thereby causing increased resistance and friction within the system). As a result, the power of the electric motor 140 required to power the system may be from about one (1) watt to about ten (10) watts or from about two (2) watts to about seven (7) watts, or from about three (3) watts to about six (6) watts, or from about four (4) watts to about five (5) watts. In other embodiments, the electric motor 140 may also run within other suitable power ranges.

Other Drive System Embodiments

Figure 19:
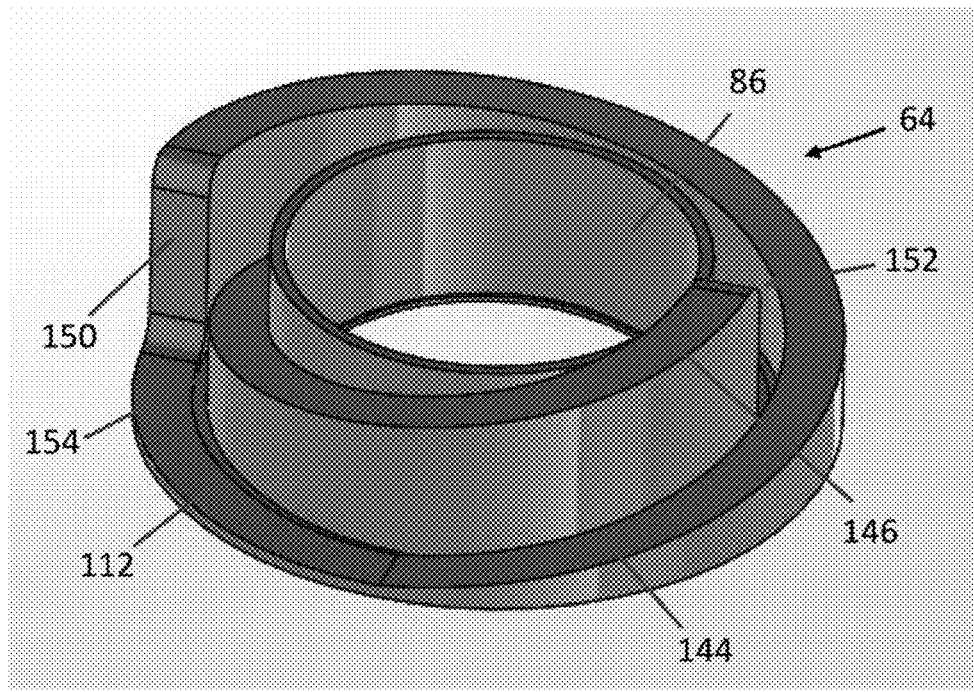
FIG. 19 illustrates a perspective view of a drive system dual ramp rotorcam, according to aspects of the present embodiments.

FIG. 19 illustrates a perspective view of a rotorcam 64 in a dual ramp configuration, according to aspects of the present embodiments. The rotorcam 64 may include an outer ramp 144, as well as an inner ramp 146 radially disposed within the outer ramp 144 (and disposed radially outward of the rotorcam center bore 86). The outer and inner ramps 144, 146 may include outer and inner drop-offs 150, 152 disposed 180-degrees apart from each other. The outer and inner ramps 144, 146 may also include outer and inner flat portions 112, also disposed 180-degrees apart from each other. In the embodiment of FIG. 19, each of the flat portions 112 span approximately 90-degrees of the circumference of the rotorcam 64, while the inclined portions of each of the outer and inner ramps 144, 146 span approximately 270-degrees of the circumference of the rotorcam 64. In other embodiments, each of the flat portions 112 may span from about 0-degrees to about 60-degrees of the circumference of the rotorcam 64, while the inclined portions of each of the outer and inner ramps 144, 146 may span from about 300-degrees to about 360-degrees of the circumference of the rotorcam 64. In other embodiments, each of the flat portions 112 may span from about 60-degrees to about 90-degrees of the circumference of the rotorcam 64, while the inclined portions of each of the outer and inner ramps 144, 146 may span from about 270-degrees to about 300-degrees of the circumference of the rotorcam 64.

Referring still to FIG. 19, the rotorcam 64 may also include a thin radial gap 154 disposed radially outward of the inner ramp 146 and radially inward of the outer ramp 144. Each of the outer and inner ramps 144, 146 may be sloped such that the increase in height as a function of the circumferential angle (or rotation) of the rotorcam 64 is constant. Stated otherwise, each of the outer and inner ramps 144, 146 transitions from a minimum height (i.e., at the flat portion 112) to a maximum height (i.e., just before each drop-off 150, 152) through a rotation of about 270-degrees. As such, the increase in height as a function of angle is constant for both the outer and inner ramps 144, 146. As a result, the increase in height as a function of distance traveled on each ramp is higher on the inner ramp 146 than on the outer ramp 144 since the inner ramp 146 increases the same overall height over a shorter distance.

Figure 20:
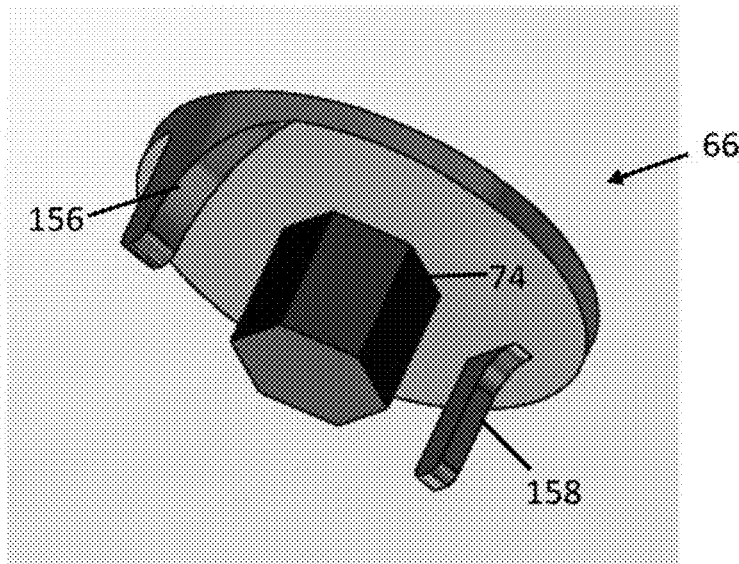
FIG. 20 illustrates a perspective view of a drive system dual cam-follower, according to aspects of the present embodiments.

FIG. 20 illustrates a perspective view of a cam follower 66 in a dual tooth configuration, according to aspects of the present embodiments. The dual-tooth cam follower 66 of FIG. 20 may include an outer tooth 156 as well as an inner tooth 158 disposed at a smaller radius than the outer tooth 156, and circumferentially spaced approximately 180-degrees from the outer tooth 156. Each of the outer and inner teeth 156, 158 are disposed radially outward of the hexagonal shaft 74. In addition, each of the outer and inner teeth 156, 158 are disposed at radii that correspond with those of the outer and inner ramps 144, 146 of the rotorcam 64 of FIG. 19. As such, the outer tooth 156 of FIG. 20 is disposed at the same radius as the outer ramp 144 of FIG. 19, while the inner tooth 158 is disposed at the same radius as the inner ramp 146. In operation, because both the outer and inner teeth 156, 158 interface with at least one of the outer and inner ramps 144, 146, the longitudinal forces acting on the cam and follower system may be more evenly distributed in a dual-tooth/dual-ramp configuration than in a single-tooth/single ramp configuration. Tri-tooth/tri-ramp, quad-tooth/quad-ramp, and other configurations are also possible, in accordance with the present embodiments.

Figure 21:
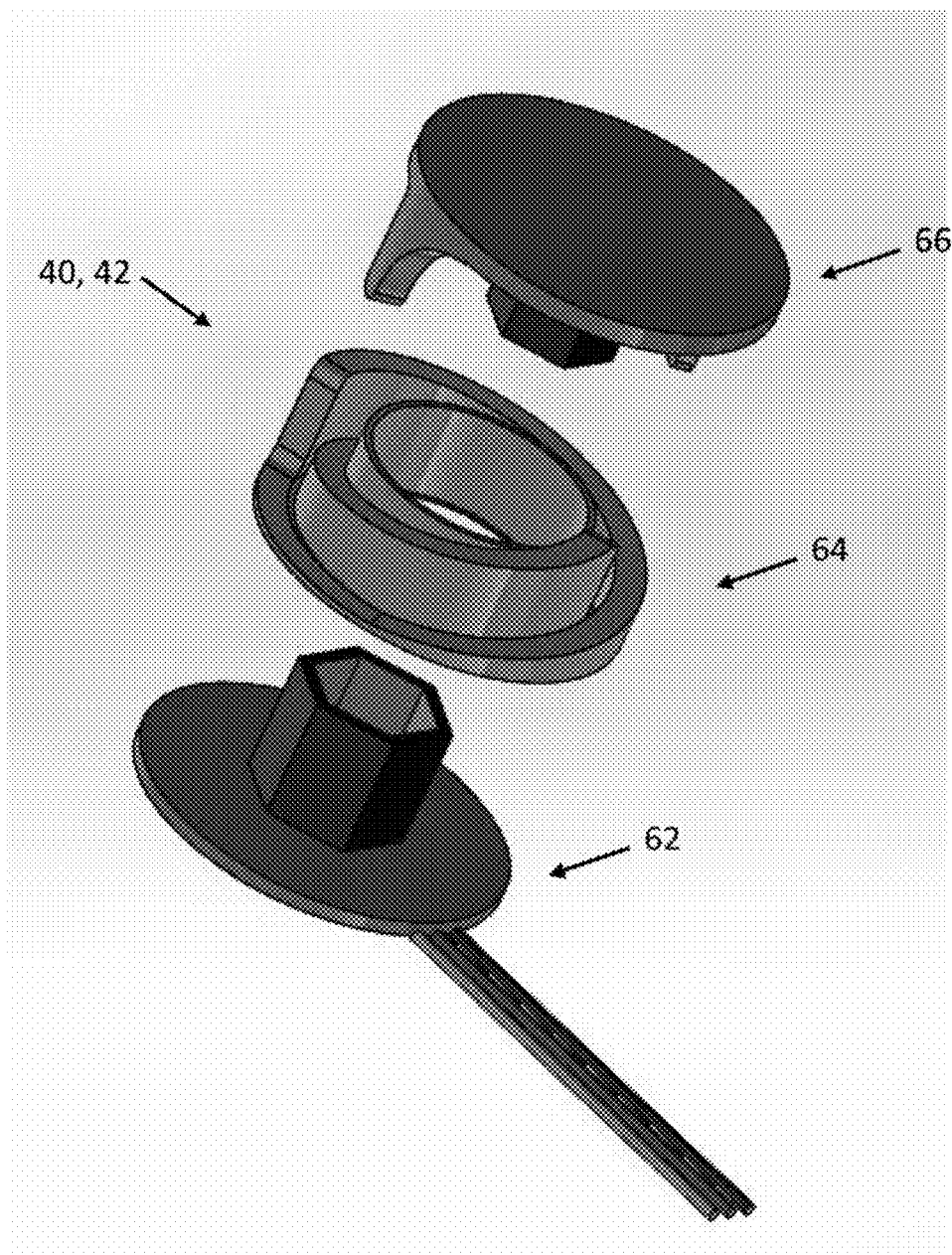
FIG. 21 illustrates a perspective view of a disassembled drive system, according to aspects of the present embodiments.

FIG. 21 illustrates a perspective view of a disassembled drive system 40, 42 in a dual ramp/dual tooth configuration including the stator assembly 62, the rotorcam 64, and the cam follower 66, according to aspects of the present embodiments.

Figure 22:
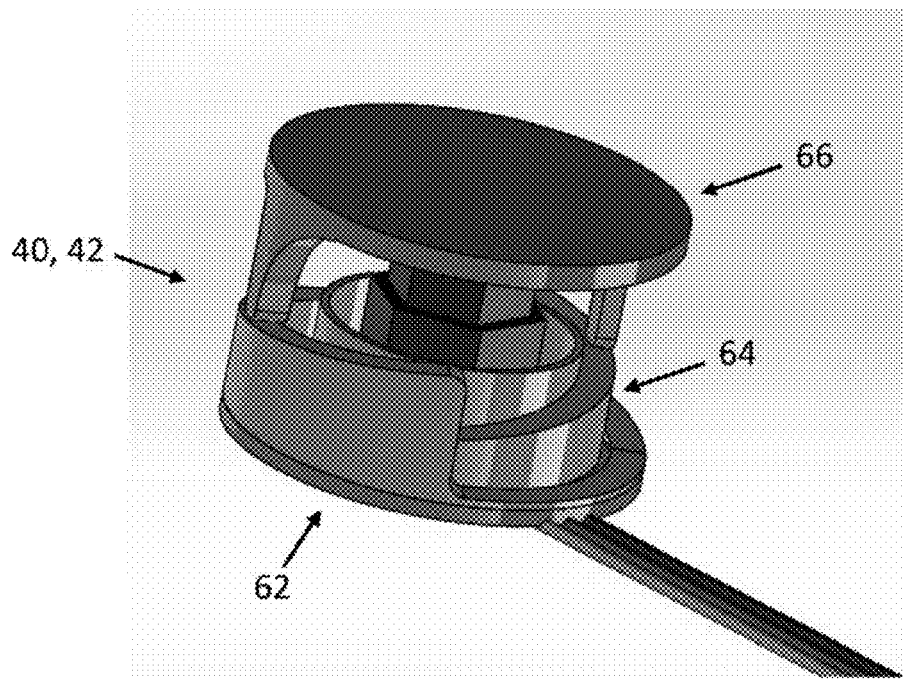
FIG. 22 illustrates a perspective view of an assembled drive system, according to aspects of the present embodiments.

FIG. 22 illustrates a perspective view of an assembled drive system 40, 42 in a dual ramp/dual tooth configuration including the stator assembly 62, the rotorcam 64, and the cam follower 66, according to aspects of the present embodiments.

Figure 23:
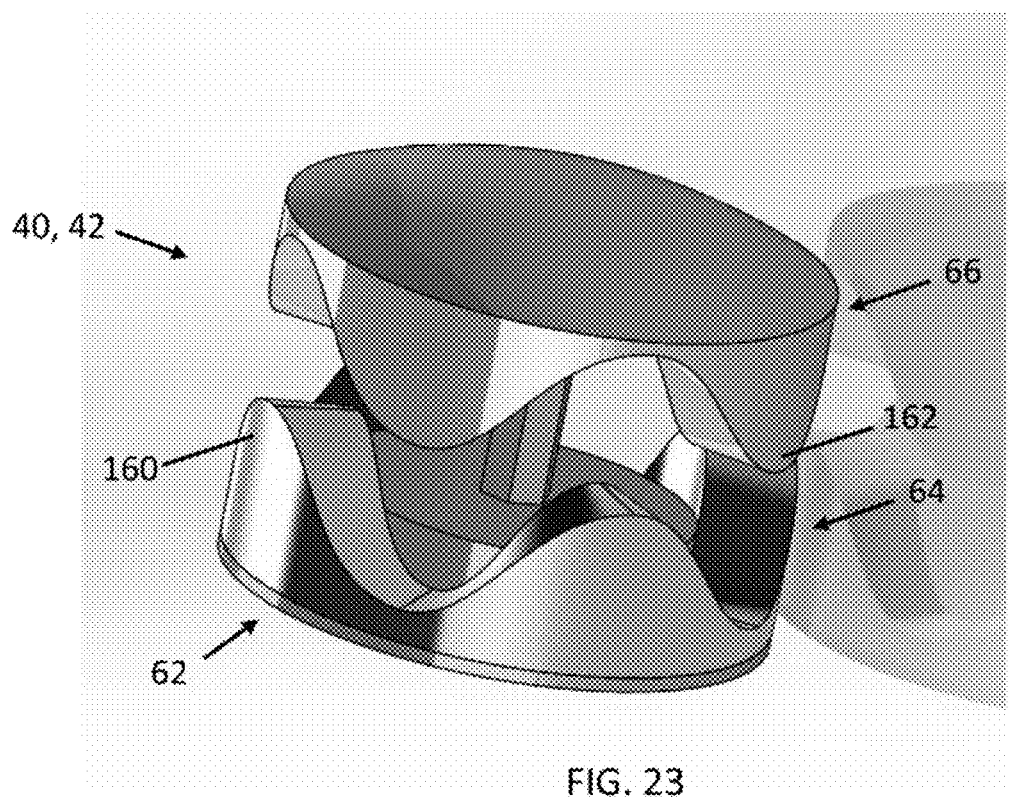
FIG. 23 illustrates a perspective view of an assembled emperor crown drive system, according to aspects of the present embodiments.

FIG. 23 illustrates a perspective view of an assembled drive system 40, 42 in an emperor crown configuration including the stator assembly 62, the rotorcam 64, and the cam follower 66, according to aspects of the present embodiments. In the embodiment of FIG. 23, the rotorcam 64 may include one or more cam lobes 160, each cam lobe 160 being contoured such that the rotorcam 64 raises the cam follower 66 as the rotorcam 64 rotates. The cam follower 66 may include one or more follower lobes 162, each follower lobe 162 being shaped and spaced to approximately match the contouring of the cam lobes 160. In the embodiment of FIG. 23, the rotorcam 64 includes four (4) cam lobes 160 while the cam follower 66 includes four (4) follower lobes 162. In other embodiments, each of the rotorcam 64 and cam follower 66 may include one (1), two (2), three (3), four (4), five (5), six (6), and higher numbers of cam lobes 160 and/or follower lobes 162. In one or more embodiments, each of the cam follower lobes 162 may include one or more rollers (not shown) to help facilitate movement of the rotorcam lobes 160 there under. A low friction, wear-resistant coating may also be disposed on each of the cam and follower lobes 160, 162 to minimize contact friction between the rotorcam 64 and the cam follower 66.

Power Supply and Charging System

Figure 24:
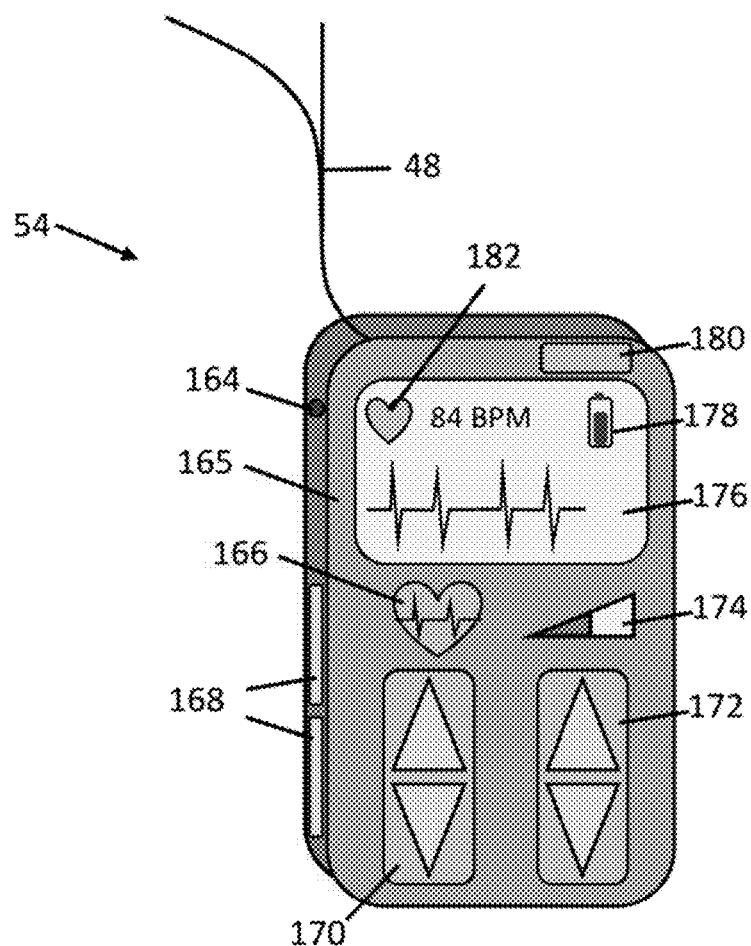
FIG. 24 illustrates a perspective view of a control module, according to aspects of the present embodiments.

FIG. 24 illustrates a perspective view of a mobile power supply 54 according to aspects of the present disclosed embodiments. The mobile power supply 54 may be electrically coupled to one or more wires 48 (or groups of wires) for supplying power to the electric motor assemblies 140 of each of the drive systems 40, 42. The mobile power supply 54 may also include a mobile power supply housing 165 and at least one external charging port 164 (for example, for plugging the mobile power supply 54 directly into a wall power outlet) disposed within the housing 165. The mobile power supply 54 may also include one or more battery ports 168 disposed in the housing 165 for inserting rechargeable batteries into the mobile power supply 54. In the embodiment of FIG. 24, the mobile power supply 54 includes two (2) battery ports 168, which allows at least one battery to be installed in the mobile power supply 54 to provide power thereto at all times, even while a second battery is being charged. The external charging port 164 may be used, in one or more embodiments and/or use cases, to simultaneously power the drive systems 40, 42, while also charging the batteries. The mobile power supply 54 may also include a heartrate control module 166 including a first set of control buttons 170 for adjusting (i.e., increasing or decreasing) the heartrate. In accordance with the present embodiments, each heartbeat may be defined as one complete cycle of the cam follower 66 rising up a rotorcam 64 ramp 70, then falling off the drop-off 88 (which corresponds to the contraction and expansion of the right and/or left ventricle 32, 34). As such, in a single tooth/single ramp embodiment (i.e., similar to FIG. 9), the drive system 40, 42 will create one heartbeat for each 360-degree rotation of the rotorcam 64. Similarly, in a dual tooth/dual ramp embodiment (i.e., similar to FIGS. 21 and 22) the drive system 40, 42 will create one heartbeat for each 360-degree rotation of the rotorcam 64. In other dual tooth/dual ramp embodiments in which each ramp 70 spans one-hundred and eighty (180) degrees and both teeth 72 interface with (and are disposed over) both ramps 70, the drive system 40, 42 will create two heartbeats for each 360-degree rotation of the rotorcam 64. The heartrate, then, as it applies to the total artificial heart system 60 of the present embodiments, is simply the number of heartbeats (as defined above) per minute.

Referring still to FIG. 24, in order to increase the cardiac output of the system, the patient may use the first set of control buttons 170 to increase (or alternatively decrease) the heartrate of the total artificial heart 30. The mobile power supply 54 may also include a volume control module 174 including a second set of control buttons 172 for adjusting (i.e., increasing or decreasing) the volume (that is, the volume of pumped blood) of each heartbeat. For example, by allowing the cam follower 66 to travel all the way to the bottom of the drive system 40, 42 (i.e., near the base 50), each of the right and left ventricles 32, 34 may expand to a larger volume,
thereby allowing more blood to flow in to each of the right and left ventricles 32, 34, to be pumped to the pulmonary or circulatory systems. As such, both the heartrate control module 166 and the volume control module 174 may be used to increase or decrease the overall cardiac output (or production). The mobile power supply 54 may also include a display screen 176 for displaying various data and information such as one or more battery charge levels 178, a heartrate indication 182, as well as other information. The mobile power supply 54 may also include a wireless communications module 180 allowing the mobile power supply 54 to wirelessly connect to Wi-Fi-enabled devices and/or network-connected devices such as smart phones, laptops, tablets, desktop computers, networks, servers, chargers, and/or other devices. The mobile power supply 54 may also include one or more clips, bands, or other connection features (not shown) enabling wearing (for example by clipping to a belt) and carrying of the mobile power supply 54. By including various features in the mobile power supply 54, the mobile power supply 54 includes an integral control interface operatively coupled to the motor assembly 140 and/or the stator assembly 62.

Figure 25:
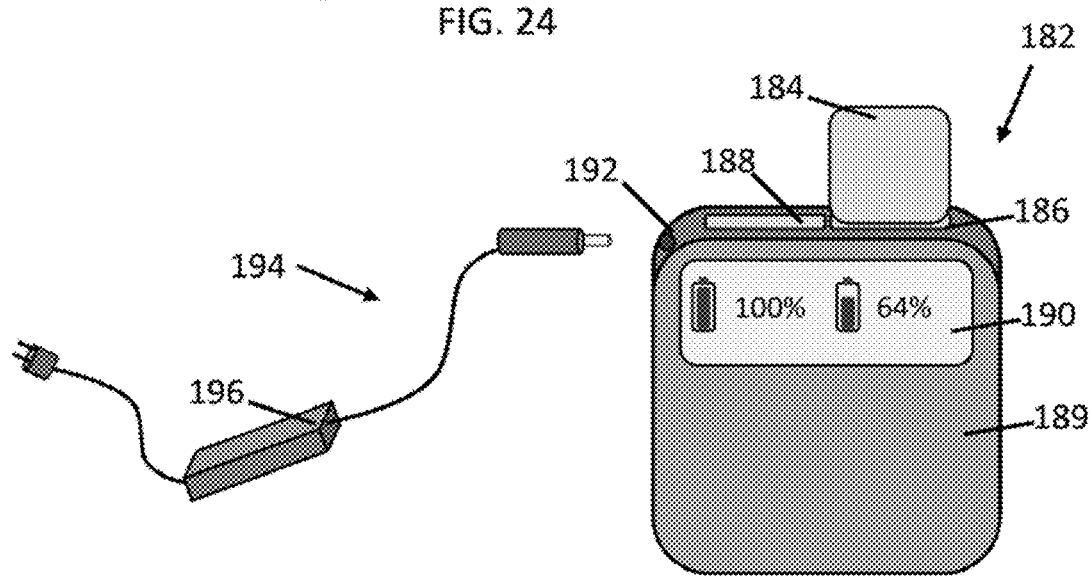
FIG. 25 illustrates a perspective view of a battery charging system, according to aspects of the present embodiments.

FIG. 25 illustrates a perspective view of a charging system 182, in accordance with the present disclosed embodiments. The charging system 182 may at least one housing 189 including first battery port 186 and a second battery port 188 for receiving one or more rechargeable batteries 184, and for electrically coupling them with an external power supply 194. The external power supply 194 may include one or more alternating current (AC) to direct current (DC) converters 196 such that the external power supply 194 can receive AC power (for example, from a wall outlet) and also supply DC power to the total artificial heart 30 via the one or more batteries 184. The charging system 182 may include one or more charging ports 192 disposed within the housing 189 for plugging in the external power supply 194. The charging system 182 may also include a display screen 190 disposed within the housing 189 for displaying data and other information such as the charge levels of the one or more batteries 184.

Figure 26:
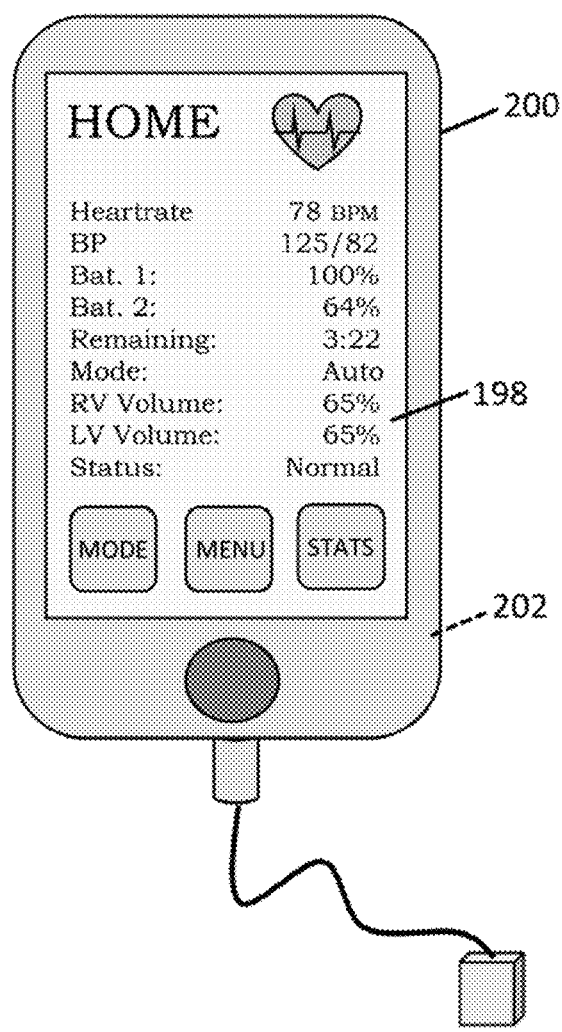
FIG. 26 illustrates a front view of a mobile device application, according to aspects of the present embodiments.

FIG. 26 illustrates a front view of application software 198 that may be displayed on one or more electronic devices such as a smart phone, desktop computer, laptop computer, tablet, and/or other device 200. The application software 198 may display such information as the heartrate, the blood pressure, a first and second battery charge level, the remaining time until both batteries are depleted (i.e., remaining life of the one or more batteries), a control mode, a right and left ventricle pumping volume, as well as an overall system status (for example, such as normal, alert, caution, etc.). A communication module 202 of the electronic device 200 may be communicatively coupled to the communication module 180 of the mobile power supply 54 such that data and information from the mobile power supply 54 may be transmitted to the electronic device 200 (for example wirelessly) in real-time or near-real time (for example in 1, 5, 10, 20, 30, or 60 second increments, etc.). The application software 198 may also include one or more buttons including (but not limited to) a mode button, a stats button (for example, to retrieve statistical operational data), as well as a menu button. The mode button may allow a user to select a control mode such as: 1) maintaining a constant heartrate and varying only the pumped volume of blood within the right and left ventricles 32, 34 when a change in cardiac output is desired; 2) maintaining a constant volume and changing the heartrate when a change in cardiac output is desired; or 3) changing both the volume and the heartrate in a "hybrid" mode of operation.

Referring still to FIG. 26, the application software 198, via the communication coupling with the mobile power supply 54, may (in one or more embodiments) allow the user to change the operation of the total artificial heart 30 directly from the electronic device 200. For example, the application software may enable a user to choose other modes of operation indicative of an overall patient level of activity such as "resting," "moderate," and/or "active." The electronic device 200 may then send a signal to the mobile power supply 54 (which in many embodiments also acts as a control unit and/or a control interface) to increase the cardiac output (for example by increasing the heartrate) when a user has selected an "active" mode of operation. The application software 198 may also include a mode of operation that allows the cardiac output to automatically follow a patient breathing rate, which may be determined via one or more accelerometer or motion sensors 82 (shown in FIG. 4) disposed within the mobile power supply 54 that sense the expansion and contraction of the lungs, stomach, and/or body cavity or diaphragm via direct contact (for example, when the mobile power supply 54 is attached to a belt of the patient). Stated otherwise, by using one or more accelerometer or motion sensors 82 mounted near a patient's waist to determine how quickly or vigorously a patient is breathing, an overall activity level of the patient may be determined and/or approximated, and a cardiac output may accordingly be adjusted to match the patient breathing rate. The application software 198, in one or more embodiments, may also be run on multiple devices simultaneously such that a friend or family member of the patient and/or a remote monitoring team can monitor the patient's status, and take appropriate action if an emergency or potentially problematic operating condition arises.

Figure 27:
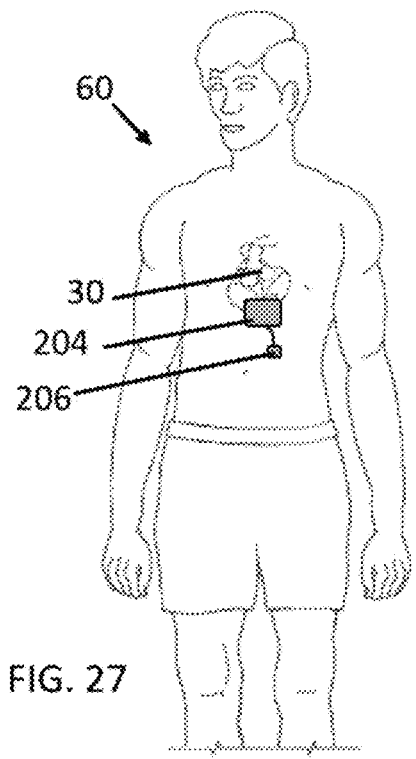
FIG. 27 illustrates a front view of an implanted total artificial heart system, according to aspects of the present embodiments.

FIG. 27 illustrates a front view of a total artificial heart system 60 according to aspects of the present embodiments. In the embodiment of FIG. 27, the total artificial heart system 60 may include an implanted total artificial heart 30 including one or more drive systems (in accordance with the present embodiments) electrically coupled to an implanted power supply 204. The implanted power supply 204 may include one or more rechargeable batteries implanted within the patient, and housed, for example, in the thicker base 50 illustrated in FIG. 16. The implanted power supply 204 may be connected to one or more external charging ports 206, which is external to the body. The external charging port allows the implanted power supply 204 to be recharged by connecting an external power supply or charger (such as those illustrated in FIGS. 4, 24, and/or 25) to the external charging port 206. By implanting a power supply 204 within the patient, the patient is afforded periods of time when he or she may be completely disconnected from an external power supply, thereby enabling periods of even greater flexibility for the patient.

Operational Characteristics

FIG. 28 illustrates a schematic of an electrical current versus volume of blood characteristic, according to aspects of the present embodiments. As the volume of blood VB being pumped increases, the electrical current drawn by the motor 140 IM also increases. The relationship between VB and IM is approximately linear, but may vary based also on the heartrate, as well as based on small variation in the blood temperature (which generally will be maintained within a narrow temperature range by the human body). As the temperature of the blood changes, even slightly, small changes in the viscosity of the blood (and thus the power required to pump the blood) may also occur. The chemistry of the blood, which may also vary over time, may also have minor effects on the viscosity of the blood. Thus, data is expected to accumulate in scattered clusters (which may be approximately linear), similar to a first cluster 208 illustrated in FIG. 28 (i.e., rather than in a strictly linear fashion). If the cluster shifts over time such that data now accumulates in a second cluster 210 where more electrical current IM is required to pump the same volume of blood VB, it may be an indication that either the drive system 40, 42 (or other component of the total artificial heart 30) has degraded and is now operating less efficiently, or possibly that the blood pressure of the patient has increased, thereby causing increased resistance to flow, and requiring additional motor power to pump the same volume of blood. As such, alerts can be triggered and appropriate action can be taken if the IM versus VB cluster has shifted over time. The motor current IM may be measured at the motor assembly 140, or at the mobile power supply 54, while the volume of blood VB being pumped each heartbeat may be derived from the minimum and maximum volumes of air in the drive system 40, 42, which may be calculated directly from the distance between proximity sensors 118, 120 (shown in FIG. 9). The volume of blood VB being pumped each heartbeat may also be approximated from the input control setting (i.e., the volume of blood that is pumped each heartbeat, as selected at the volume control module 174 of the mobile power supply 54 (FIG. 24)).

FIG. 29 illustrates a schematic of volume of air versus pressure of air characteristic, according to aspects of the present embodiments. The volume of the air VA within the drive system 40, 42 may be determined using the one or more proximity sensors 118, 120, while the pressure of the air PA may be determined via the at least one pressure sensor 113 (shown in FIG. 10). Because the drive system 40, 42 is a closed, air-tight system, the pressure of air may also be derived from the volume of the air within the drive system 40, 42 VA using Boyle's law (or ideal gas law), $PV=nRT$, where P is the pressure, V is the volume, n is the number of air molecules (which is constant and doesn't change), R is a constant, and T is approximately constant since the human body temperature is maintained within a narrow temperature range. Therefore, pressure and volume (as it applies to the air in the drive system 40, 42) are more or less inversely proportional to one another, and one may be approximated directly from the other. As the volume goes up, the pressure goes down. As the volume goes down, the pressure goes up. Curve 212 (shown in FIG. 29) illustrates the volume vs pressure characteristic for air in the drive system 40, 42 when the system is set to pump a smaller volume of blood. In the operating condition corresponding the curve 212, because the cam follower 66 does not drop all the way to the bottom portion 100, the volume of air (i.e., under the cam follower 66) does not get squeezed down as much. As a result, the drive system 40, 42 goes from the maximum volume of air down to a medium volume of air, back to a maximum volume of air (and the air pressure correspondingly goes from a minimum pressure to a medium pressure, back to a minimum pressure). In the operating condition corresponding to curve 214, the drive system 40, 42 is set to allow the cam follower 66 to drop all the way down to the bottom portion 100, thereby squeezing the air down to a minimum volume and allowing each of the right and left ventricles 32, 34 to expand to a maximum volume (corresponding to a maximum cardiac output). In the operating condition corresponding to curve 214, the drive system 40, 42 goes from the maximum volume of air down to a minimum volume of air, back to a maximum volume of air (and the air pressure correspondingly goes from a minimum pressure to a maximum pressure, back to a minimum pressure).

Referring still to FIG. 29, the pressure and volume may be inversely proportional in a strictly linear relationship under steady-state conditions (that is, assuming a constant temperature). However, under typical operating conditions of the drive system 40, 42, the volume is continuously changing and thus the conditions are never truly steady-state. As such, the pressure may lag the volume slightly, at least as sensed by the one or more pressure sensors 113. Stated otherwise, as the volume changes, it takes time for the pressure to "catch-up" such that the pressure sensor 113 "reacts" and sends a signal reflective of the new pressure. This pressure sensor 113 time lag is reflected by the elliptical shape of the curves 212, 214, 216, 218, 220, and 222 in FIGS. 29-31. In other embodiments, the volume vs. pressure relationship may be represented as strictly linear and inversely proportional. Arrows on one or more of the curves indicate how the volume versus pressure relationship changes when the system is in operation.

FIG. 30 illustrates a schematic of a volume of blood versus pressure of blood characteristic, according to aspects of the present embodiments. The volume of the blood VB within each of the right and left ventricles 32, 34 may be determined using the volume of the air VA within the drive system 40, 42 (to which it is inversely proportional). The overall volume of the total artificial heart 30 is constant (or approximately constant) so as the volume of air in the drive system 40, 42 increases, the volume of blood in the right and left ventricles 32, 34 must decrease. Similarly, as the volume of air in the drive system 40, 42 decreases, the volume of blood in the right and left ventricles 32, 34 must increase. The pressure of the blood PB may be determined based on the volume of blood VB in each of the right and left ventricles 32, 34 using an inverse relationship. When the volume of blood in the right and left ventricles 32, 34 is at a maximum value (as marked by a first point "A" in FIGS. 29 and 30) the volume of the air VA within the drive system 40, 42 will be at a minimum value. Similarly, when the volume of blood in the right and left ventricles 32, 34 is at a minimum value (as marked by a second point "B" in FIGS. 29 and 30) the volume of the air VA within the drive system 40, 42 will be at a maximum value. As such, curve 218 (in FIG. 30) corresponds to a resting condition when the total artificial heart 30 is pumping the minimum amount of blood, while curve 216 of FIG. 30 corresponds to an active (or maximum cardiac output) condition when the total artificial heart 30 is pumping the maximum amount of blood.

FIG. 31 illustrates a schematic of a volume of air VA versus pressure of air PA characteristic, according to aspects of the present embodiments. In the embodiment of FIG. 31, if the VA versus PA characteristic shifts from an initial curve 220 to a new curve 222 such that for a given volume, there is additional air pressure, it could be an indication that something has changed in the total artificial heart system 60. For example, because the amount of air and the volume ranges of the system do not change over time, a shift in the VA versus PA characteristic similar to that of FIG. 31 may be an indicator that external pressure is acting on the drive system 40, 42 (for example, due to increased blood pressure acting on the diaphragm 36, 38 and/or follower dome 110), thereby indicating that mitigating action should be taken (for example, the patient should visit the doctor, or have his or her blood pressure checked using a separate system such as a sphygmomanometer).

Figure 32:
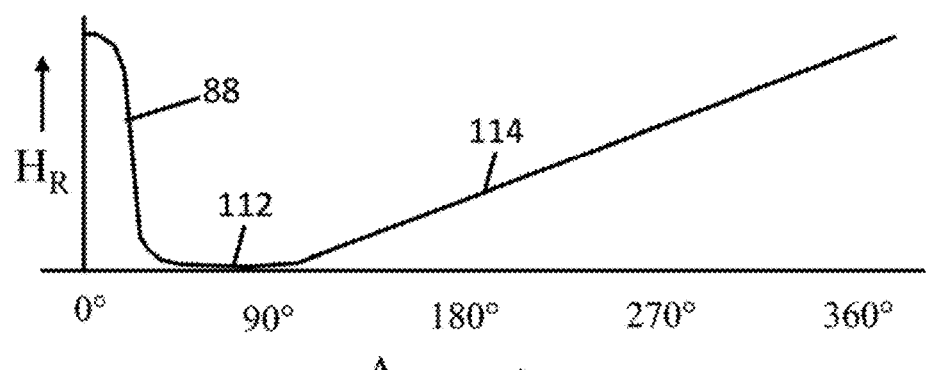
FIG. 32 illustrates a schematic of ramp height versus rotor angle characteristic, according to aspects of the present embodiments.

FIG. 32 illustrates a schematic of ramp height HR versus rotor angle AR characteristic, according to aspects of the present embodiments. The ramp height HR varies at any given fixed circumferential location as the rotorcam 64 rotates through various rotor angles AR. For example, at a rotor angle AR of zero (0) degrees, the ramp height HR may be at a maximum. As the rotorcam 64 rotates to ninety (90) degrees such that the drop-off 88 passes under the one or more teeth 72, the ramp height is at a minimum value (for example, at the flat portion 112). As the rotorcam 64 rotates to one hundred and eighty (180) degrees, two-hundred and seventy (270) degrees, and eventually to three-hundred and sixty (360) degrees, the ramp height HR steadily increases on the inclined portion 114, eventually reaching a maximum height at three-hundred and sixty (360) degrees (or zero (0) degrees).

Figure 33:
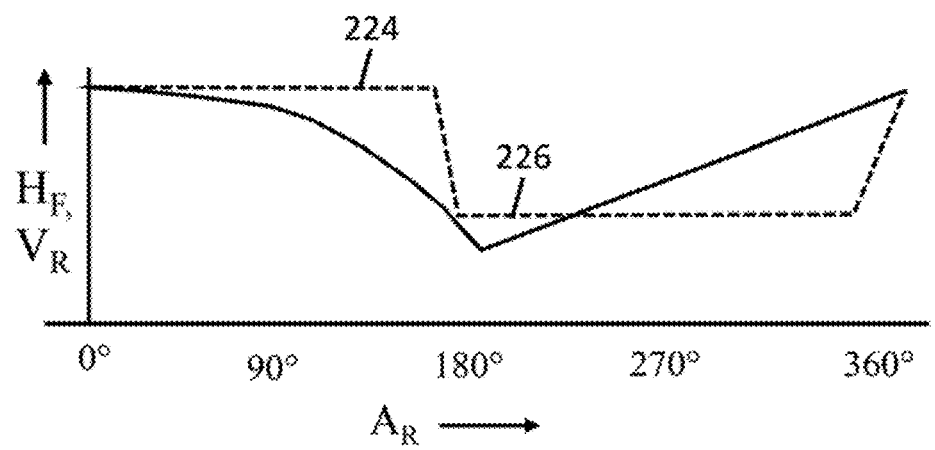
FIG. 33 illustrates a schematic of both follower height and rotor velocity versus rotor angle characteristic, according to aspects of the present embodiments.

FIG. 33 illustrates a schematic of both follower height HF and rotor velocity VR versus rotor angle AR characteristics, according to aspects of the present embodiments. The illustration of FIG. 33 assumes a system with the same ramp height HR profile as that of FIG. 32. In the embodiment of FIG. 33, the rotor velocity VR (as represented by the dashed line) is at higher velocity 224 from about zero (0) degrees to about one-hundred and eighty (180) degrees, and at a lower velocity 226 from about one-hundred and eighty (180) degrees to about three-hundred and sixty (360) degrees. The electric motor 140 may control the rotational speed, even within a single rotation, based on the Hall sensor 118, 120 data (i.e., which can be used to determine both rotational speed VR and circumferential location of the rotorcam 64). As the drop-off 88 of the rotorcam 64 passes under the one or more teeth 72, the rotorcam 64 is rotating at the higher velocity 224. As a result, the tooth 72 does not make contact with the ramp 70 until the rotorcam 64 has rotated about one-hundred and eighty (180) degrees. Stated otherwise, the height of the follower HF drops from zero (0) degrees to one-hundred and eighty (180) degrees, but because the rotorcam 64 is spinning so quickly, the cam follower 66 never touches the flat portion 112. Instead, the cam follower 66 first makes contact with the ramp 70 (i.e., after the drop-off 88 passes) at the inclined portion 114. Because the cam follower 66 is not dropping all the way down in the embodiment of FIG. 33, the volume of the right and left ventricles 32, 34 never reaches a maximum value. Accordingly, the embodiment of FIG. 33 corresponds to a resting or minimum cardiac output condition.

Figure 34:
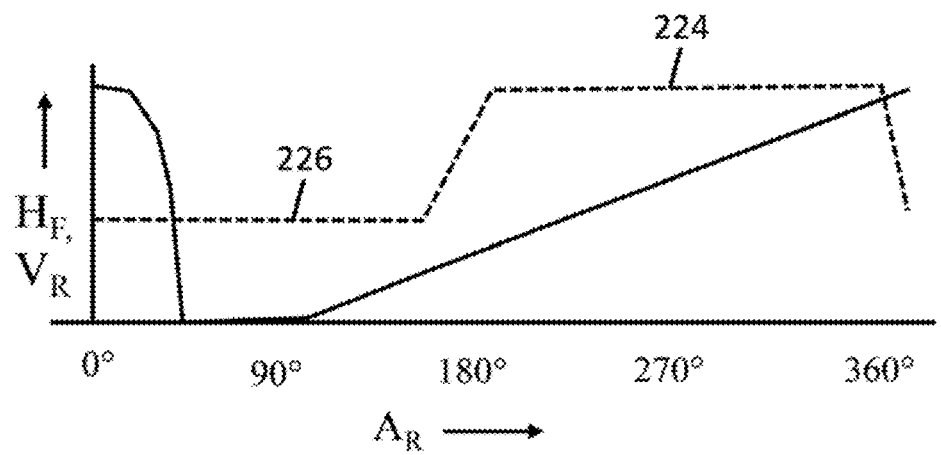
FIG. 34 illustrates a schematic of both follower height and rotor velocity versus rotor angle characteristic, according to aspects of the present embodiments.

FIG. 34 illustrates a schematic of both follower height HF and rotor velocity VR versus rotor angle AR characteristics, according to aspects of the present embodiments. The illustration of FIG. 34 assumes a system with the same ramp height HR profile as that of FIG. 32 (and also FIG. 33). In the embodiment of FIG. 33, the rotor velocity VR (as represented by the dashed line) is at a lower rotational velocity 226 from about zero (0) degrees to about one-hundred and eighty (180) degrees, and at a higher rotational velocity 224 from about one-hundred and eighty (180) degrees to about three-hundred and sixty (360) degrees. As the drop-off 88 of the rotorcam 64 passes under the one or more teeth 72, the rotorcam 64 is rotating at the lower velocity 226. As a result, the tooth 72 drops down and makes contact with the flat portion 112. Stated otherwise, the height of the follower HF drops down much more quickly in the embodiment of FIG. 34, than that of FIG. 33. Because the cam follower 66 is dropping all the way down in the embodiment of FIG. 34, the volume of the right and left ventricles 32, 34 does reach a maximum value. Accordingly, the embodiment of FIG. 34 corresponds to an active or maximum cardiac output condition.

Referring to FIGS. 33 and 34, the area above the follower height HF curve (i.e., the solid curve) is directly proportional to the cardiac output of the total artificial heart 30. As such, the lower the cam follower 66 drops, the higher the cardiac output of the total artificial heart 30 will be. The cam follower 66 will drop down more quickly as the rotational speed between zero (0) degrees and about one-hundred and eighty (180) degrees is decreased. The rotor angle AR may also be described as a circumferential orientation of the rotorcam 64. In the embodiments of both FIGS. 33 and 34, the average rotational speed across the full three-hundred and sixty (360) degree rotation may be identical. However, in FIG. 33, the rotorcam 64 rotates quicker during the first portion of the rotation, resulting in a lower overall cardiac output. By contrast, in FIG. 34, the rotorcam 64 rotates slower during the first portion of the rotation, resulting in a higher overall cardiac output. Stated otherwise, the magnitude of the expansion of the right and/or left artificial ventricle 32, 34 is inversely proportional to the rotational speed of the rotorcam 64. As such, the cardiac output can be adjusted higher and lower by adjusting the rotational speed within each rotation, without changing the overall average rotational speed (i.e., or heartrate).

Each of the operational characteristics illustrated in FIGS. 28-34 may be used (individually and/or in concert with one another) to detect changes in one or more conditions related to the patient's health. For example, if any of the operational characteristics illustrated in FIGS. 28-34 changes over time, an alert may be sent to the patient and/or a clinician indicating that the patient's blood pressure has changed, or that one or more potentially harmful conditions such as hypervolemia, pulmonary hypertension, blood clot, and others may exist.

Methods of Operation

Figure 35:
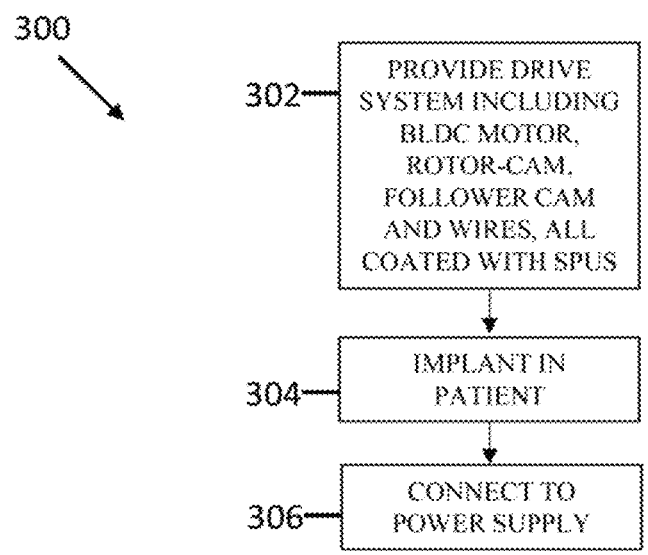
FIG. 35 illustrates a schematic of a method of implanting a total artificial heart, according to aspects of the present embodiments.

FIG. 35 illustrates a schematic of a method 300 of implanting a total artificial heart 30 in a human body, according to aspects of the present embodiments. At step 302, the method 300 may include providing a system including an electric motor (such as a BLDC motor 140) including a stator assembly 62, a rotorcam 64, a cam follower 66, and wires 48, where at least one of the system components is coated with a segmented polyurethane solution (SPUS). At step 304, the method 300 may include implanting the system into a patient. At step 306, the method 300 may include connecting a power supply to the implanted system.

Figure 36:
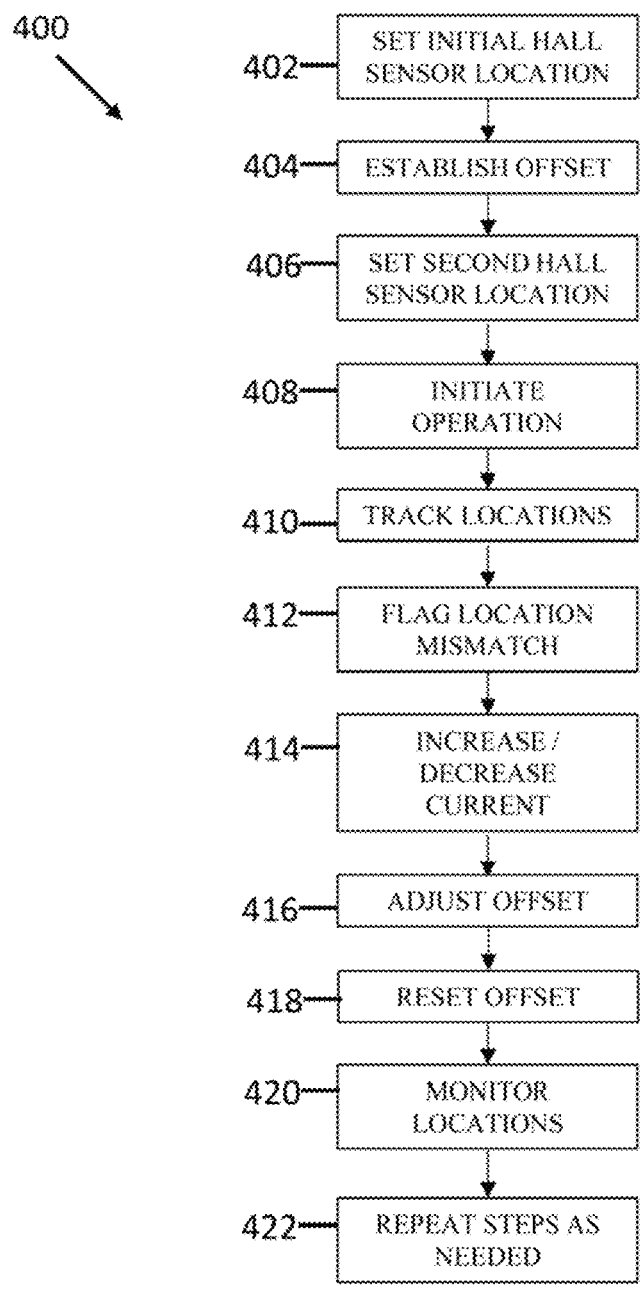
FIG. 36 illustrates a schematic of a method of calibrating a total artificial heart, according to aspects of the present embodiments.

FIG. 36 illustrates a schematic of a method 400 of calibrating a total artificial heart 30, according to aspects of the present embodiments. At step 402, the method 400 may include setting an initial Hall sensor 136 location within the rotorcam 64 or the stator assembly 62 such that the Hall sensor 136 may detect changes in the electromagnetic field associated with each rotation of the rotorcam 64. At step 404, the method 400 may include establishing an offset between a first drive system 40 and a second drive system 42 such that the right and left ventricles 32, 34 may be actuated (or pumped) in an ordered fashion with a contraction of the right ventricle 32 immediately following the contraction of the left ventricle 34 (or vice versa). In other embodiments, the offset may be established by rotationally offsetting the rotorcam 64 within the second drive system 42 from that of the first drive system 40 (i.e., set them at different initial angles) such that even though electricity may be introduced to each drive system simultaneously, the first and second drive systems 40, 42 will be at different portions of the pumping cycle. At step 406, the method 400 may include setting a second Hall sensor 136 location corresponding to the location of the second rotorcam 64 (i.e., the rotorcam 64 of the second drive system 42). At step 408, the method 400 may include placing the total artificial heart 30 in operation. At step 410, the method 400 may include tracking the locations of each of the rotorcams 64 within the respective first and second drive systems 40, 42 such that the offset may be monitored. At step 412, the method may include flagging (or sending an alert indicating) when the initial offset has drifted. At step 414, the method 400 may include slightly increasing or decreasing the electrical current (thereby controlling the rotational speed) to one of the two drive systems 40, 42 (while maintaining the other one at a constant value) thereby adjusting the offset (at step 416) to a new value, or resetting the offset (at step 418) back to the initial value. At step 420, the method may include monitoring the locations of each rotorcam 64 (and the angular offset therebetween) to determine if a change in the offset has occurred. At step 422, the method 400 may include repeating any of steps 402-420 as needed, in order to achieve a desired rotorcam 64 offset and/or calibration of the system.

Figure 37:
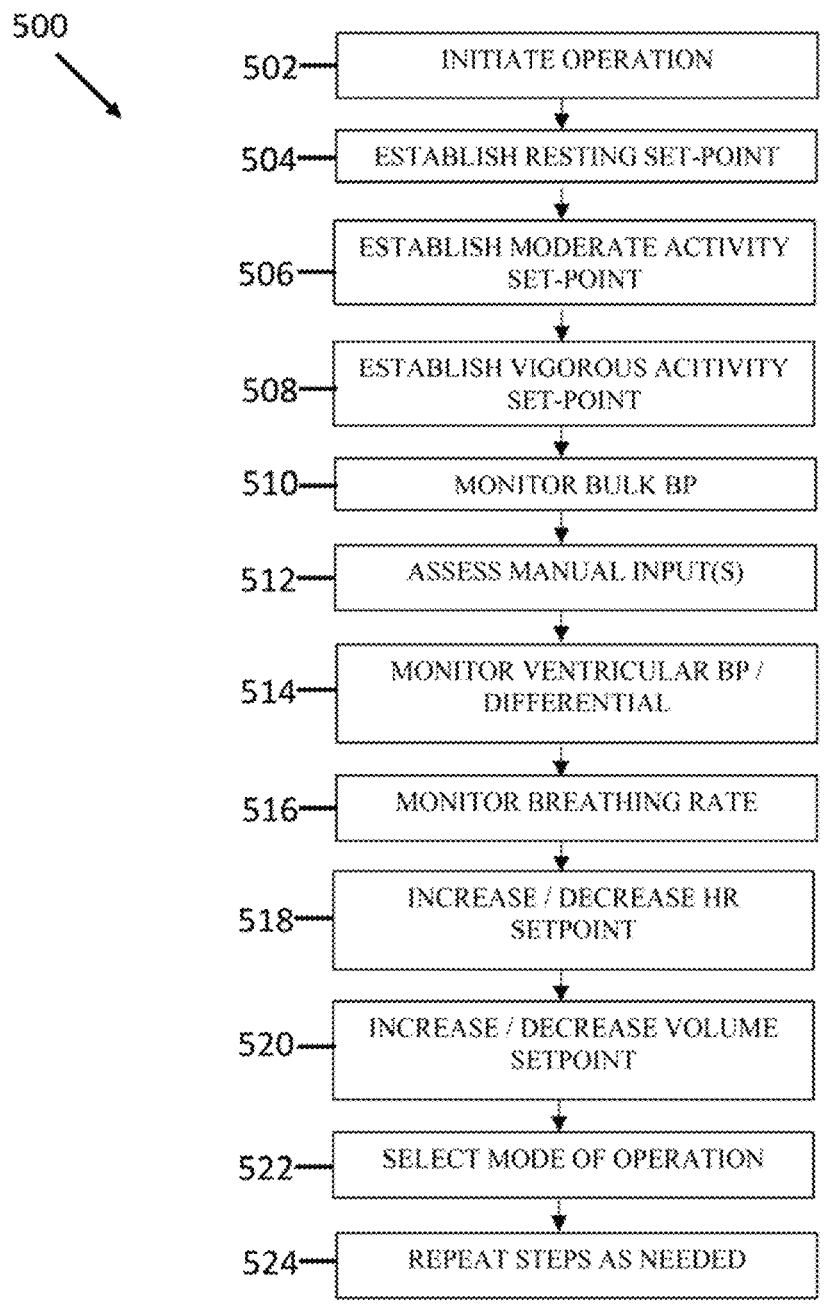
FIG. 37 illustrates a schematic of a method of operating a total artificial heart, in accordance with aspects of the present disclosed embodiments.

FIG. 37 illustrates a schematic of a method 500 of operating a total artificial heart 30, in accordance with aspects of the present disclosed embodiments. At step 502, the method 500 may include initiating operation of the total artificial heart system 60. At step 504, the method 500 may include establishing a resting set-point (for example a resting heartrate, a resting blood volume, and/or a resting compression ratio of the drive system 40, 42). At step 506, the method 500 may include establishing a moderate activity set-point (i.e., corresponding to the desired cardiac output associated with moderate activity). At step 508, the method 500 may include establishing a vigorous activity set-point (for example setting a heartrate, blood volume, or compression ratio that corresponds to the desired cardiac output for vigorous activity). At step 510, the method 500 may include monitoring a bulk blood pressure (for example, as determined via FIGS. 28-31, or via a separate device such as a sphygmomanometer). At step 512, the method 500 may include assessing manual inputs that the patient or user may have made at the control interface or mobile power supply 54 (i.e., at the heartrate control module 166 or the volume control module 174), for example to increase or decrease the cardiac output (i.e., from one of the setpoints). At step 514, the method 500 may include monitoring the blood pressure within each of the right and left artificial ventricles 32, 34 so as to determine if there is a difference between the two (which may be indicative, for example, of pulmonary hypertension or a blood clot). At step 516, the method 500 may include monitoring the breathing rate via the one or more accelerometer or motion sensors 82 mounted near a patient's waist (i.e., in order to assess if a cardiac output should be increased, for example, to match an elevated patient breathing rate). At step 518, the method 500 may include increasing or decreasing one or more heartrate set-points so as to adjust the cardiac output to a desired level based on a breathing rate, a manual input, a bulk blood pressure, a ventricular blood pressure differential, and/or another factor. At step 520, the method 500 may include increasing or decreasing one or more blood volume set-points so as to adjust the cardiac output to a desired level based on a breathing rate, a manual input, a bulk blood pressure, a ventricular blood pressure differential, and/or another factor. At step 522, the method 500 may include selecting a different mode of operation (for example, manual, resting, moderate exercise, breathing rate matching, vigorous exercise, hybrid control, and/or another control mode). At step 524, the method 500 may include repeating any of steps 502-522 as needed to achieve a desired mode of operation of the total artificial heart system 60.

Referring to FIGS. 35-37, each of the methods 300, 400, 500 may include steps not illustrated in the respective figures. In addition, in one or more embodiments of each of the methods 300, 400, 500, the steps may be performed in a different order than what is illustrated. In other aspects of the present embodiments, each of the methods 300, 400, 500 may also omit one or more steps. In one or more embodiments, each of the methods 300, 400, 500 may include performing at least one step concurrently with at least one other step.

The present disclosed embodiments provide a total artificial heart system 60 that enables enhanced flexibility for patients. By providing power from an external power source 54 to an implanted internal electric motor assembly 140 that powers a drive system 40, 42, the external hardware that needs to be carried and managed by the patient can be reduced. Aspects of the present disclosed embodiments include a lightweight external power supply 54 that can be worn on a belt or carried in a pocket, thereby freeing up both hands. In addition, the external power supply may include a convenient control interface allowing the user to easily replace batteries, as well as to adjust the operation of the total artificial heart system 60 as needed. The drive system 40, 42 of the present embodiments converts the rotational motion of the electric motor to a linear motion, and saves space by shaping the external rotating "rotor" of the electric motor in such a way that it itself forms the rotating "cam" which pushes the "cam follower" in a linear motion, thus combining the functions of a cam in a cam and follower system with the functions of a rotor in a rotor/stator electrical motor system, resulting in a single rotorcam component. By using an electric motor 140 that is selectively controlled such that any rotational speed can be dialed in at any angle within the rotation, and then by using a cam and follower system to translate rotational motion into linear motion, the contraction and expansion of the chambers of the heart may be controlled both quickly and gently as needed at each and every point within each rotation of the rotorcam (and within each heartbeat). The drive system 40, 42 of the present embodiments includes three (3) primary components including the stator assembly 62, the rotorcam 64, and the cam follower 66, thereby reducing complexity and enhancing durability of the system. The drive mechanism has a "pusher" that now mechanically pushes the ventricle diaphragm during systole. And, the drive mechanism detaches mechanically at the start of diastole, allowing the body to naturally fill the ventricle. Additionally, a spring and damper optionally may be used in order to help with ventricle filling during diastole. And, because the system is now driven by electric motors that fit inside the artificial ventricles, it is possible that the system (batteries and controller) may be now fully implanted. In addition, the biocompatible materials and coatings of aspects of the present embodiments ensure that patients will not have an undesirable response or reaction to the implanted components.

Each of the instruments, devices, and sensors described in the present disclosure may include a wired power supply or a wireless power supply such as a battery, capacitor, or other suitable mechanism.

Elements of different implementations described may be combined to form other implementations not specifically set forth previously. Elements may be left out of the processes described without adversely affecting their operation or the operation of the system in general. Furthermore, various separate elements may be combined into one or more individual elements to perform the functions described in this specification.

Other implementations not specifically described in this specification are also within the scope of the following claims.

These and other features, aspects and advantages of the present invention will become better understood with reference to the foregoing description and appended claims. The accompanying drawings, which are incorporated in and constitute a part of this specification, illustrate embodiments of the present disclosure and, together with the description, serve to explain the principles of the present embodiments.

In order for the present disclosure to be more readily understood, certain terms are first defined below. Additional definitions for the following terms and other terms are set forth throughout the specification.

An apparatus, composition, or method described herein as "comprising" one or more named elements or steps is open-ended, meaning that the named elements or steps are essential, but other elements or steps may be added within the scope of the composition or method. To avoid prolixity, it is also understood that any apparatus, composition, or method described as "comprising" (or which "comprises") one or more named elements or steps also describes the corresponding, more limited composition or method "consisting essentially of" (or which "consists essentially of") the same named elements or steps, meaning that the composition or method includes the named essential elements or steps and may also include additional elements or steps that do not materially affect the basic and novel characteristic(s) of the composition or method. It is also understood that any apparatus, composition, or method described herein as "comprising" or "consisting essentially of" one or more named elements or steps also describes the corresponding, more limited, and closed-ended composition or method "consisting of" (or "consists of") the named elements or steps to the exclusion of any other unnamed element or step. In any composition or method disclosed herein, known or disclosed equivalents of any named essential element or step may be substituted for that element or step.

As used herein, "a" or "an" with reference to a claim feature means "one or more," or "at least one."

As used herein, the term "left" is interpreted in a frame of reference taken from the patient's perspective, which may be opposite the location in which it appears on the page. For example, in FIG. 2, the left artificial ventricle 34 is located on the right side of the Figure.

As used herein, the term "right" is interpreted in a frame of reference taken from the patient's perspective, which may be opposite the location in which it appears on the page. For example, in FIG. 2, the right artificial ventricle 32 is located on the left side of the Figure.

As used herein, the term "substantially" refers to the qualitative condition of exhibiting total or near-total extent or degree of a characteristic or property of interest.

It is to be understood that while the disclosure has been described in conjunction with the detailed description thereof, the foregoing description is intended to illustrate and not limit the scope of the invention(s). Other aspects, advantages, and modifications are within the scope of the claims.

This written description uses examples to disclose the invention, including the best mode, and also to enable any person skilled in the art to practice the present embodiments, including making and using any devices or systems and performing any incorporated methods. The patentable scope of the present embodiments is defined by the claims, and may include other examples that occur to those skilled in the art. Such other examples are intended to be within the scope of the claims if they include structural elements that do not differ from the literal language of the claims, or if they include equivalent structural elements with insubstantial differences from the literal languages of the claims.

What is claimed is:

1. A total artificial heart (TAH) system comprising:
    at least one artificial ventricle configured to be coupled to at least one of a pulmonary artery, a vessel of a heart, and a chamber of a heart;
    at least one drive system that comprises at least one electric motor that is coupled to the at least one artificial ventricle and that is configured to cause a volume of the at least one artificial ventricle to contract and expand; and
    at least one power supply electrically coupled to the at least one electric motor, wherein the at least one artificial ventricle and the at least one drive system are configured to be implanted in the chest cavity of a patient;
    wherein the at least one drive system comprises:
    a stator assembly;
    a rotorcam mechanically and electrically coupled to the stator assembly; and
    a cam follower mechanically coupled to both the stator assembly and the rotorcam, and
    wherein at least one of the following conditions is satisfied:
    (1A) the TAH system comprises at least one spring coupling the cam follower to the stator assembly and, when the stator assembly comprises a housing with a shaped cross-section:
        the cam follower comprises a shaft with a shaped cross-section matching the shaped cross-section of the housing,
        each of the shaped cross-section of the housing and the shaped cross-section of the shaft comprises at least one of a triangular cross-section, a square cross-section, an elliptical cross-section, a pentagonal cross-section, a hexagonal cross-section, and a rectangular cross-section, and
        the shaft is disposed within the housing;
    (1B) the rotorcam comprises:
        a center bore that is concentric about a centerline of the rotorcam; and a ramp radially disposed around the center bore and including at least one of a drop-off, an inclined portion, and, when the ramp includes both the drop-off and the inclined portion, the ramp further includes a flat portion disposed between the inclined portion and the drop-off; and/or the cam follower comprises at least one tooth extending toward the rotorcam and interfacing with at least one portion of the ramp;

(1C) the rotorcam comprises at least one of neodymium iron boron (Nd—Fe—B), iron, cobalt, samarium cobalt (Sm—Co), aluminum, alnico, bonded Nd—Fe—B, magnetite, ceramic (hard ferrite), ferrite, gadolinium, one or more rare earth elements, strontium, barium, and iron (III) oxide;

(1D) the TAH system further comprises at least one proximity sensor that is disposed within at least one of the stator assembly and the cam follower and that is configured to detect a relative position of the cam follower with respect to the stator assembly;

(1E) the TAH system further comprises at least one pressure sensor disposed on at least one of the stator assembly and the rotorcam;

(1F) the rotorcam comprises a center bore of the rotorcam, wherein the stator assembly comprises a cylindrical housing, and wherein the cylindrical housing is disposed within the center bore of the rotorcam such that rotorcam extends circumferentially around, and radially outward of, the cylindrical housing; and (1G) the stator assembly comprises a cylindrical housing of the stator assembly, wherein the rotorcam is disposed about the cylindrical housing of the stator assembly, and wherein the system is configured to cause a change in a height of the cam follower with rotation of the rotorcam about the cylindrical housing of the stator assembly, wherein, when the cam follower is coupled to the at least one artificial ventricle, the change in the height of the cam follower causes contraction or expansion of the volume of the at least one artificial ventricle.

2. A TAH system according to claim 1, wherein:

(2A) when the condition (1A) is satisfied, the shaft is configured to move longitudinally within the housing of the stator assembly, and/or wherein the housing of the stator assembly includes at least one damper disposed within said housing of the stator assembly, and/or (2B) when the condition (1F) is satisfied, the rotorcam further comprises a retaining rim disposed around a top of the cylindrical housing, said retaining rim being configured to allow the rotorcam to rotate about the cylindrical housing and to prevent the rotorcam from translating longitudinally.

3. A TAH system according to claim 1, wherein at least one of the following conditions is satisfied:

(3A) the at least one electric motor comprises a brushless direct current (BLDC) motor;

(3B) the at least one electric motor comprises at least one Hall sensor;

(3C) the at least one electric motor comprises at least six winding groups;

(3D) a plurality of winding groups present in the at least one electric motor is disposed radially outward of an inner stator housing of the at least one electric motor;

(3E) a winding group present in the at least one electric motor comprises one or more longitudinally aligned conductive coil wires;

(3F) the inner stator housing of the at least one electric motor comprises a hexagonal housing and an outer stator housing of the at least one electric motor comprises a cylindrical housing; and (3F) a rotor of the at least one electric motor comprises at least one permanent magnet.

4. A TAH system according to claim 1, wherein the at least one power supply includes a mobile power supply, and further comprising: an electronic device that includes
at least one display screen;
application software for tracking an activity of at least one TAH system; and
at least one communications module configured to wirelessly communicate at least one data parameter between the electronic device and the mobile power supply.

5. A TAH system according to claim 4, wherein the at least one artificial ventricle includes a right artificial ventricle and a left artificial ventricle, and wherein the TAH system is configured to satisfy at least one of the following conditions:

(5A) the TAH system is configured to display at least one data parameter transmitted from the mobile power supply to the electronic device on the at least one display screen;

(5B) the at least one data parameter comprises at least one of a heartrate and a blood pressure of the patient in whom the at least one total artificial heart system has been implanted;

(5C) the at least one data parameter comprises at least one of a charge level and a remaining life of at least one battery operationally coupled to the mobile power supply;

(5D) when the at least one artificial ventricle and the at least one drive system have been implanted in the patient, the at least one data parameter comprises at least one of a blood volume of the right artificial ventricle a blood volume of the left artificial ventricle, an operating mode of the total artificial heart system, and an operating status of the total artificial heart system; and (5E) the electronic device is configured to communicate with an auxiliary electronic device on which the application software is installed.

\* \* \* \* \*